United States Patent [19]

Gordon et al.

[11] Patent Number: 5,486,452

[45] Date of Patent: Jan. 23, 1996

[54] DEVICES AND KITS FOR IMMUNOLOGICAL ANALYSIS

[75] Inventors: Julian Gordon, Arlesheim; Richard Hawkes, Allschwil, both of Switzerland; Evelyn Niday, Arlington Heights, Ill.; Harry Towbin, Allschwil, Switzerland

[73] Assignee: Ciba-Geigy Corporation, Ardsley, N.Y.

[21] Appl. No.: 38,470

[22] Filed: Apr. 10, 1987

Related U.S. Application Data

[63] Continuation of Ser. No. 912,144, Sep. 24, 1986, abandoned, which is a continuation of Ser. No. 673,211, Nov. 19, 1984, abandoned, which is a continuation of Ser. No. 345,440, Feb. 3, 1982, abandoned.

[30] Foreign Application Priority Data

| Apr. 29, 1981 | [GB] | United Kingdom | 8113167 |
| Nov. 13, 1981 | [GB] | United Kingdom | 8134353 |
| Jan. 18, 1982 | [GB] | United Kingdom | 8201289 |

[51] Int. Cl.$^6$ ............... G01N 33/548; G01N 33/564; G01N 33/569

[52] U.S. Cl. ............... 435/5; 435/7.1; 435/7.2; 435/7.21; 435/7.22; 435/7.23; 435/7.31; 435/7.32; 435/7.7; 435/7.72; 435/7.9; 435/7.91; 435/7.92; 435/7.94; 435/7.95; 435/970; 435/975; 436/506; 436/507; 436/509; 436/518; 436/530; 436/807; 436/821

[58] Field of Search ............... 436/506, 507, 436/509, 518, 530, 807, 821, 810; 435/7.1–7.23, 7.31, 7.32, 7.7, 7.72, 7.9–7.95, 970, 975

[56] References Cited

U.S. PATENT DOCUMENTS

| 3,654,090 | 4/1972 | Schuurs et al. | 195/103.5 |
| 3,979,509 | 9/1976 | Giaever | 436/518 |
| 4,020,151 | 4/1977 | Bolz et al. | 424/1.5 |
| 4,048,298 | 9/1977 | Niswender | 424/1.5 |
| 4,071,315 | 1/1978 | Chaten | 436/518 |
| 4,119,589 | 10/1978 | Horn et al. | 260/6 |
| 4,139,346 | 2/1979 | Rabbani | 436/504 |
| 4,168,146 | 9/1979 | Grubb et al. | 23/230 B |
| 4,176,174 | 11/1979 | Russell | 436/513 |
| 4,189,464 | 2/1980 | Blumberg et al. | 424/1 |

(List continued on next page.)

FOREIGN PATENT DOCUMENTS

| 0027008 | of 1981 | European Pat. Off. . |
| 0050424 | 4/1982 | European Pat. Off. . |
| 2074061 | of 1971 | France . |
| 2257259 | of 1975 | France . |
| 1235686 | 6/1971 | United Kingdom . |
| 1235685 | 6/1971 | United Kingdom . |
| 1486826 | of 1977 | United Kingdom . |
| 1526708 | 9/1978 | United Kingdom . |
| 1553083 | 9/1979 | United Kingdom . |
| 1597345 | 9/1981 | United Kingdom . |
| 1601283 | 10/1981 | United Kingdom . |

OTHER PUBLICATIONS

Derwent Abstract 72923X/39.
Derwent Abstract 10866B/06.
Derwent Abstract 50464C/29.
Derwent Abstract 84–051476/09.
Archives of Biochemistry & Biophysics 71:377–385 (1957).
Archives of Biochemisty & Biophysics 71:386–392 (1957).
Biochimica Et Biophysica Acta 78:516–528 (1963).
Ann. Rev. Microbiol. 33:413–437 (1979).

(List continued on next page.)

*Primary Examiner*—David Saunders
*Attorney, Agent, or Firm*—Irving M. Fishman; Karen G. Kaiser

[57] ABSTRACT

New devices and kits for solid-phase immuno-assays comprising a solid porous support, preferably in the form of a sheet, where antigens or immuno-globulins or both of them are bound by direct application in any suitable geometry, e.g. as an assay of dots or lines. Such porous supports are suitable for effecting an unlimited number of antibody-antigen reactions simultaneously and in one operation.

47 Claims, 1 Drawing Sheet

The standards give three gradations of color intensity: ●, ⊗, ⊘.
Antigen spots are matched with the corresponding standard intensity.

U.S. PATENT DOCUMENTS

| | | | |
|---|---|---|---|
| 4,200,690 | 4/1980 | Root et al. | 435/7 |
| 4,216,245 | 8/1980 | Johnson | 422/57 |
| 4,267,270 | 5/1981 | Stout | 435/7 |
| 4,275,053 | 6/1981 | Rosenfield | 436/531 |
| 4,302,204 | 11/1981 | Wahl | 435/6 |
| 4,305,720 | 12/1981 | Bernstein | 436/518 |
| 4,305,721 | 12/1981 | Bernstein | 436/518 |
| 4,332,283 | 6/1982 | Pernice et al. | 436/506 |
| 4,358,535 | 11/1982 | Falkow | 435/5 |
| 4,378,344 | 3/1983 | Zahradnik | 435/531 |
| 4,407,943 | 10/1983 | Cole et al. | 436/528 |
| 4,407,943 | 10/1983 | Cole | 436/528 |
| 4,414,324 | 11/1983 | Stout | 435/7 |
| 4,436,824 | 3/1984 | Bishop | 436/529 |
| 4,452,901 | 6/1984 | Gordon et al. | 436/530 |
| 4,459,360 | 7/1984 | Marinkovich | 436/530 |
| 4,591,570 | 5/1986 | Chang | 436/518 |

OTHER PUBLICATIONS

Clinica Chimica Acta 102:169–177 (1980).

The Journal of Biological Chemistry vol. 254: 12240–12247 (1979).

Pizzolata et al, J. Immunol. Methods 26:365–368 (1979).

Towbin et al, Proc. Natl. Acad. Sci. U.S.A. 76 4350–4354 (1979).

Bowen, B. et al, *Nucleic Acids Research*, vol. 8(1), pp. 1–20 (Jan. 1980).

Renart, J. et al, *Proc. Natl. Acad. Sci. USA,* vol. 76(7), pp. 3116–3130 (1979).

Wahl, G. M. et al, *Proc. Natl. Acad. Sci. USA,* vol. 76(8), pp. 3683–3687(1979).

Katafos, F. C. et al, *Nucleic Acids Research,* vol. 7(6) pp. 1541–1552 (1979).

Moseley, S. T. et al, *J. of Infectious Diseases,* vol. 142(6), pp. 892–898 (Dec. 1980).

Gugerli, P. Revue Suisse Agric, vol. 11, No. 6, pp. 253–260 (1979).

Owens, R. A. and Diener T. O., Science, vol. 213, pp. 670–672 (1981).

Brandsna J. & Miller G. Proceedings National Academy Sciences, vol. 77, No. 11, pp. 6851–6855 (1980).

Anderson D. et al, *Methods in Enzymology,* vol. 68, pp. 428–441 (1979).

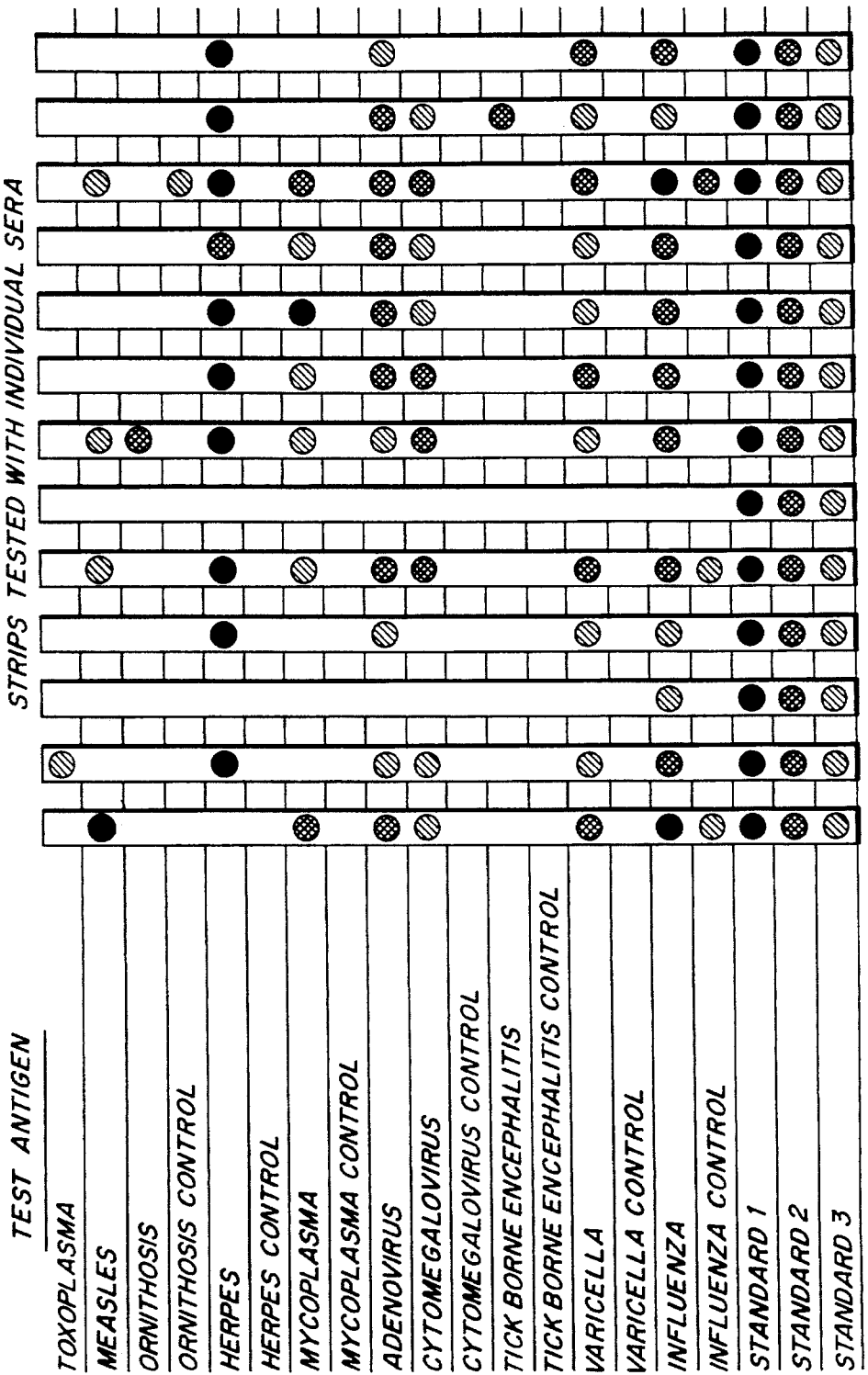

DEVICES AND KITS FOR IMMUNOLOGICAL ANALYSIS

This application is a continuation of application Ser. No. 06/912,144, filed Sep. 24, 1986 and now abandoned, which is a continuation of application Ser. No. 06/673,211; filed Nov. 19, 1984 and now abandoned, which is a continuation of application Ser. No. 06/345,440, filed Feb. 3, 1982 and now abandoned.

The present invention concerns new devices for immunological analysis, a process for their preparation, and their use, especially for multi-parameter antibody analysis and for the screening of hybridomas making monoclonal antibodies.

Tests depending directly or indirectly on the measurement of antibodies in the serum of the blood of patients are widely used in clinical diagnosis. Depending on the individual antibody in question, tests are in routine use depending on well-established principles: immune precipitate formation alone or combined with diffusion and/or electrophoresis, fixation of complement by antibody-antigen complexes, agglutination of erythrocytes by antibodies, or direct measurement of binding of the antibody to the antigen. All of these principles are used in one way or another in kits which are commercially available for the diagnosis of disease past or present. Thus, specific test kits are manufactured for the detection or measurement of antibodies which occur as a consequence of viral, bacterial, fungal or parasitic infections. Each test kit is custom-made for a specific antibody.

An inherent difficulty in the above mentioned pre-existing diagnostic kits is that false positive responses, unrelated to the disease, may result as a consequence of the high sensitivity of the procedures employed. Positive results are normally only significant when changes in the antibody titer can be detected during the progression of the disease. This prevents any rapid conclusion. A basal level for the antibody is never available for that patient prior to the particular disease, when the known test kits are used.

This would only become possible if a system were available which were sufficiently simple for a physician to be carried out in his private practice or in a health center, as part of routine health care, and were at the same time sufficiently versatile to be able to establish basal levels of any antibody which is either of known current clinical interest, or which might prove to be clinically interesting in the future. In such a test, data would be corrected concerning antibodies which are not obviously of immediate clinical relevance. However, since antibodies are extraordinarily specific, but not absolutely specific, rare fortuitous cross reactions will occur. This might be due to a fortuitous antigenic cross-reactive or because the disease, for unknown reasons, causes a malfunction of the immune system and the production of an irrelevant antibody. Thus, for instance, antibodies against the infecting bacterium in rheumatic fever are suspected of cross-reacting with heart muscle tissue; in infectious mononucleosis heterophilic antibodies which cross-react with and cause agglutination of erythrocytes of other species, such as horse, are used in a diagnostic kit.

The present invention, which is defined more precisely below, will obviate all these drawbacks of the existing analytical tests of antigens based on antibody detection. It will promote the discovery of the said fortuitous cross-reactivities and irrelevant antibody formation.

The invention is directed to test kits of great simplicity and programmability and which permit e.g. the establishment of a detailed "anti-body profile", which makes maximum use of information from the body's own disease-surveillance system in the diagnosis of disease. The kits comprise as the essential feature a device in the form of a solid support for antigens or immunoglobulins suitable for the immunological analysis or detection of both antibodies and antigens of any kind, for instance drugs or hormones.

We understand by the term "antibody" a specific class of protein molecules characterized by being from the immunoglobulin fraction of blood or secreted by cultured cells derived from the immune system, and having a specific reaction with a corresponding ligand referred to in the text of this application by the term "antigen".

Primarily, the present invention concerns a new device for immunological analysis consisting of a porous solid support containing an array of delimited adsorption areas of antigens, and/or of immunoglobulins, obtainable by applying aliquots of solutions or suspensions of one or more antigens or said immunoglobulins by direct contact to the support.

The absorbed areas of antigens or immunoglobulins on said solid supports can be maintained in a suitable state for reaction with antibodies or antigens, respectively, contained in a liquid, for instance a serum, which has to be analyzed, also after drying and storing the support. The invention is thus especially directed to this dried form of said device. However, before carrying out the desired immuno-assays, all the adsorption capacities for proteins on the surface of the porous support in the zones not covered by the antigens or immunoglobulins applied, and also inside these zones, must be saturated by treating the surface with non-specific proteins or sera containing such proteins. Also during this treatment the antigens or immunoglobulins originally applied are maintained intact so as to preserve the antigen-antibody reaction, and will remain so also upon drying and storing.

A second aspect of the present invention thus is a device consisting of a porous solid support containing an array of delimited adsorption areas of antigens, and/or immunoglobulins, obtained by applying aliquots of solutions or suspensions of one or more antigens or said immunoglobulins by direct contact to the support, and further treated with excess of non-specific proteins so as to block all the residual adsorption capacities of the adsorbing surface. By non-specific proteins are meant such proteins which do not cross react with the specific antibodies which are expected to be in the serum to be analyzed, and which are also different from the antigens applied to the porous support. A device so prepared for direct use in immuno-assays, especially in the dried form, which can be stored and used long after its manufacture, is of particular importance.

A third aspect of the present invention is a new method for immunological analysis comprising the use of both the preceding devices.

In a fourth aspect the invention comprises the manufacture of devices as defined above, consisting in applying aliquots of solutions or suspensions of one or more antigens and/or immunoglobulins, by direct contact to the support.

In a fifth aspect the invention concerns the manufacture of kits, comprising the devices in the form of the solid supports above mentioned, together with prepared reagents and equipment for executing the immunological assays.

The present invention is based on the finding that antigens or immunoglobulins can be applied by direct contact of the liquids containing them to the solid porous support so as to obtain delimited adsorption areas, which can be, if desired, as restricted as possible, by suitably limiting the volumes of liquids to be applied; that the areas so obtained do not spread out on the surface; and that the antigens or immunoglobulins adhere very tightly to the porous surface and can be maintained unaltered for practically an indeterminate time, and are suitable for reaction with antibodies or with antigens respectively in biological liquids, and for their detection by any of the known immunological assay methods. For example, when the device comprises antigens bound to a solid support, bound antibodies may be detected with the use of an (indicator) antibody, such as a radioactively labeled (indicator) antibody or an (indicator) antibody coupled with an enzyme giving a color reaction. By the term "indicator" a molecule which has a group attached to it which generates a detectable and measurable signal under specified conditions, is understood.

It has also been found that these immunological assays can be carried out even with extremely small dots of antigens or immunoglobulins, without interferences between the various antigens or immunoglobulins mounted and foreign substances contained in the test liquids. This finding is certainly surprising when compared to the various methods for immunological assays known in the prior art, especially those mentioned above. It is especially surprising that the simple device and the method of its application according to the present invention is of very general applicability and can be used for practically all antigenic substances including e.g. proteins, nucleic acids, carbohydrates, lipids, and related substances, and any kind of immunoglobutins.

The state of the art preceding this invention, apart from the finding in the article mentioned below in Proc. Natl. Acad. Sci. USA, which represented a decisive advance in the use of microporous sheets for the performance of antibody binding assays on replicas of electropherograms, can be exemplified by U.S. Pat. No. 4,200,690 and the European patent application 27008. The U.S. patent describes a procedure for the increasing of the binding capacity of nitrocellulose microporous supports by various complicated coating procedures in unawareness of the high intrinsic binding capacity per unit area of nitrocellulose. In addition, a number of earlier patents, summed up in the said European patent application, describe the use of various kinds of geometries of plastic surfaces with convolutions, perforations, inserts, etc., to increase the binding capacity. Difficulties were described in the complete removal of excess reagents from such surfaces. An essential feature of this present invention is the high binding capacity of microporous sheets, combined with the ease of thorough washing e.g. by simply dispensing the washing fluid, e.g. with a plastic wash bottle, and pouring off excess reagent.

The said European Patent Application 27008 describes a procedure for carrying out multiple antibody-antigen reactions by the use of coated plastic tubes and inserts, in contact with the same liquid sample. While the invention of that patent purports to be capable of multiple assays simultaneously, and the merits and need for such multiple assays are extensively described, only examples for two simultaneous assays are described and more than two could hardly be performed in practice. The key feature of that invention is the physical separation of the tube and the insert following the reaction, and the counting of bound radioactivity separately. It is obvious that the number of assays performable with that invention could be increased by the use of multiple isotope techniques combined with the radio-immune assay, but it cannot be increased in practice for routine use, with the use of more than two isotopes, because of the complications of the radioactivity determinations. This would then give a maximum of 4 simultaneous assays. The examples given are also exclusively for the use in radio-immune assays. The present invention, on the other hand, makes use of the high capacity per unit area combined with the high intrinsic resolution of microporous supports, to permit an unlimited increase on the number of simultaneous assays. Furthermore, the examples of European patent application 27008 are limited to the use of specific antibodies bound to the support, intended to measure the corresponding antigens. In the present invention the use of the system is possible with an essentially unlimited number of different antigens to measure their corresponding antibodies; and also the use of the support for antibodies, which will then bind their corresponding specific antigens, and the use of specific reagents which will identify antigen-antibody complexes, such as complement components.

In the article entitled "Electrophoretic transfer of proteins from polyacrylamide gels to nitrocellulose sheets: Procedure and some applications", published in *Proc. Natl. Acad. Sci. USA*, Vol. 76, No. 9, pp. 4350–4354, September 1979, a procedure for the electrophoretic transfer of proteins from a gel to a microporous sheet and the detection of these proteins by immuno-assay procedures involving antibodies has been described. The electrophoretic transfer of the proteins give a faithful replica of the original pattern contained in the gel on a nitrocellulose sheet. The antibody assays with such transferred electropherograms are carried out after the residual adsorption capacities of the nitrocellulose sheet have been saturated by incubation with a non-specific protein, a feature which is also adopted in the present invention. The above mentioned immuno-assays with electrophoretically transferred proteins are rendered possible by the fact that no exchange takes place between the electrophoretically blotted specific proteins and the non-specific proteins used for the blocking of the residual capacity of the support. The finding of the present invention that such intact preservation of bound antigens from any interference on the part of the non-specific proteins used for the blocking of the residual adsorption sites (background adsorption) and the prolonged incubations of antibody assay is possible, also when the antigens and/or immunoglobulins are applied directly, i.e. in the absence of any electric fields, is one decisive factor for the development of the new devices and their use for antibody analysis. It is also surprising that in the further incubations with the antisera and the indicator antibody no disturbing side-reactions take place, e.g. exchange with the adsorbed non-specific proteins. Furthermore it could not be supposed that the former electrophoretic method could be perfected and put on to a quantitative basis by the simple direct application of the antigen. Because of the high resolving power of the new method when applied to supports having a great number of microdots of antigens, it is almost infinitely programmable, being at the same time of extreme simplicity in operation. Immunoglobulins can be mounted, if desired, together with antigens on the porous solid support if it is intended to make the immunological analysis of antibodies of the present invention on a quantitative basis; known amounts of immunoglobulins are applied to the solid support along with the antigens; these immunoglobulins will react with the indicator-antibody to give a detectable reaction which can be taken as a basis for comparison with the corresponding reaction of immunoglobulins bound to the antigens. The method of immunological analysis of the present invention can thus be calibrated with the use of a suitable internal standard based on known amounts of, for example, human immunoglobulins. Since the method is capable of determining large number of antibodies simultaneously, fortuitously elicited antibodies which either cross-react with some other antigen or which were not previously known to be elicited by the disease, will easily be detected. It can furthermore incorporate all known diagnostic tests depending on the determination of individual antibodies, into one universal test.

The porous support may be any material with sufficient surface porosity to allow access by immunoglobulins and a suitable surface affinity to bind antigens. Microporous structures are generally preferred, but materials with gel structure in the hydrated state can be used as well. As to their chemical nature they may be:

A) Natural polymeric carbohydrates and their synthetically modified, crosslinked or substituted derivatives, such as a) agar, agarose; cross-linked alginic acid; substituted and cross-linked guar gums, cross-linked dextran polymers and starches b) regenerated celluloses; cellulose esters, especially with nitric acid and carboxylic acids; mixed cellulose esters, cellulose ethers, especially with lower aliphatic alcohols.

B) Natural polymers containing nitrogen, such as proteins and derivatives, e.g. cross-linked or modified gelatin.

C) Natural hydrocarbon polymers, such as latexes and rubbers.

D) Synthetic polymers which can be prepared with suitably porous structures, such as a) vinyl polymers, such as polyethylene, polypropylene, polystyrene, polyvinylchloride, polyvinylacetate and its partially hydrolysed derivatives, polyacrylates, polyacrylamides, polymethacrylates b) copolymers and terpolymers of the above vinyl monomers among themselves and with other monomers c) polycondensates, such as polyesters, polyamides d) addition polymers, such as polyurethanes or polyepoxides.

E) Inorganic materials which can be prepared in a suitably porous form, such as sulfates or carbonates of alkaline earth metals and magnesium, e.g. barium sulfate, calcium sulfate, calcium carbonate, magnesium carbonate, or silicates of alkali and alkaline earth metals and/or aluminium and/or magnesium, and aluminium or silicon oxides or hydrates, such as clays, alumina, talc, kaolin, zeolite, silicagel, glass. These materials can be used as such or as fillers in one of the above polymeric materials.

F) Mixtures or co-polymers of the above classes, such as graft co-polymers obtained by initiating polymerization of synthetic polymers on a pre-existing natural polymer.

All these materials may be used as such in suitable shapes, such as films, sheets, plates, cylinders, etc. or they may be coated onto or bonded or laminated to appropriate inert carriers, such as: paper, glass, plastic films, metal foils, fabrics. The device is preferably in the form of sheets of thickness in the range from approximately 0.01 mm and 0.5 mm, preferably of about 0.1 mm. The pore size may vary within wide limits, preferably between about 0.025 and about 15 microns, especially between about 0.15 micron and about 15 microns.

The surfaces of these supports can be activated by chemical processes which cause covalent linkage of the antigens and/or immunoglobulins to the support. The irreversible binding of the antigen or antibody is obtained, however, in general, by adsorption on the porous material by poorly understood hydrophobic forces. There is preferably used a microporous cellulose ester, for instance an ester of cellulose with an aliphatic carboxylic acid, such as an alkane carboxylic acid, having from 1 to 7 carbon atoms, e.g. acetic acid, propionic acid, or any of the butyric acids or valeric acids. There may also advantageously be used, however, sheets of nitrocellulose, by which term any nitric acid ester of cellulose is intended, if desired, in mixture, with any of the said carboxylic acid cellulose esters. Thus, pure nitrocellulose esters can be used as consisting of an ester of cellulose having approximately 3 nitric groups per 6 carbon atoms. An excellent material based on nitrocellulose for making devices according to the present invention is in commerce under the Trade name "Millipore" (commercialized by the firm Millipore, Bedford, Mass, USA) and has a pore size of 0.45 microns.

The antigens or immunoglobulins are applied to the described solid support by direct contact, by which term any mechanical transfer, either manual, e.g. with capillary tubes or pipettes or syringes or by the aid of liquid or gaseous propellants, such as sprays, e.g. by a suitably directed stream of air or gas or some template or applicator miniaturized by means of procedures such as are in common practice in micro-electronics, with the use of lithographic or similar procedures, or by "charged drop" propulsion as in high-speed electronic printing, is understood. The sample can be applied so as to give any suitable geometry, the formed adsorption areas being in the form e.g. of dots, spots or lines, or any other configuration which is suitable. The array may include a great number of antigens or a few, or even a single one. There are preferably applied small volumes of the antigenic liquids or serums, for instance aliquots smaller than 1 μl, especially smaller than 0.1 μl. In this way micro-dots can be obtained on the porous surface. Micro-dots, for instance having a diameter smaller than 2 mm, especially smaller than 0.5 mm, are most suitable for crowding the maximum number of antigens, and/or immunoglobulins e.g. on a two-dimensional area or array; lines, e.g. of width of approximately 2 mm or less, e.g. 1 mm, may be most suitable for a more limited number of antigens or antibodies where the results can be readily visualized or quantitated by some mechanical scanning apparatus. Such an array of parallel lines can then be cut into many strips in a way which lends itself to mass production of the test system.

A typical test device according to the present invention for antibody-analysis of sera may be for example in the form as shown in the attached figure, which shows the dots as developed after immersion into the various sera to be analyzed and rendered visible by reaction with indicator antibodies coupled to enzymes capable of giving a color reaction with its substrate. Standards 1–3 are normal human serum in appropriate dilutions. Devices of these types may serve the purpose of carrying out "multi-parameter antibody" analysis. The case of kits having one single antigen mounted on the solid porous support is especially of importance for the screening of hybridomas making monoclonal antibodies.

The system of the new kits may be programmed without limits or restrictions, since any desired number of antigens or combinations of antigens or immunoglobulins can be included in a single test procedure and can then be analyzed in a single operation. The invention is then e.g. used to monitor concentrations of antibodies which are normally endemic, but which may vary in a pathological situation, or to detect and quantitate antibodies which are only found in a pathological situation. With the use of nitrocellulose as porous material for the support, preferably in the form of sheets, it is surprising how high the resolving power of the system is. When a sample is applied via a micro-capillary, the dot remains extremely small, in the sub-millimeter range; it does not spread out during the subsequent treatments and reactions. Such micro-dot antigen sheets can be used for detection and quantitation of an extremely wide range of antibodies in human sera.

Once the selected antigens and/or optionally immunoglobulins have been mounted in the said manner on to the solid porous support, the device must be processed further, before being usable for the immuno-assays, to block excess binding sites of the porous material. This is done by incubation of the said support containing the antigens or immunoglobulins array with non-specific proteins or with a mixture of such proteins, or with total serum, or any combination of these ingredients alone and/or together with the ingredient of the subsequent immuno-assay steps. The only limitation is that the said proteins should not interfere with or cross-react with any of the antibodies or antigens respectively in the immuno-assays, and, of course, that they be different from those mounted on the support. The blocking of these residual adsorption sites can also be made in steps. Thus, in a preliminary step the support containing the fixed antigens or antibodies can be incubated with bovine serum albumin. Such proteins are advantageously diluted in physiological saline, and the assembly incubated with them, preferably at slightly elevated temperature, for instance between 30° and 50°, preferably at 40°, and washed with physiological saline. After this preliminary treatment there may still be present protein binding sites which have not yet been completely blocked, which have also to be blocked when immuno assays have to be carried out. If there is background adsorption due to remaining binding sites or exchange of the non-specific protein, it can be prevented by carrying out the incubation with the first antiserum and that with the indicator antibody in the continued presence of the same non-specific protein and additionally in the presence of total serum, as carrier, derived from species other than those of the test antibody. The continued presence of these mixtures of proteins both blocks remaining binding sites, and tends to prevent, by competition, exchange of the antibodies with proteins previously bound to non-specific sites or non-specific interaction of any kind with immunoglobulins. The carrier serum thus used should not be from a species which contains immunoglobulins which cross-react with the indicator antibody.

In the case of an immunoassay for the detection of antibodies the device prepared as described above is e.g. incubated with the antiserum to be analyzed diluted according to the expected antibody concentration, usually in the range 1:100 to 1:10000 in blocking solution, for instance in the range of 2 hours to overnight, at room temperature, and then washed extensively with physiological saline to remove excess unbound antibodies. The indicator antibody is radioactively labeled, fluorescent or luminescent or conjugated with a fluorescent substance, or with an enzyme capable of giving a color reaction with its substrate. The indicator antibody is usually diluted about 1000-fold in a mixture of the above named blocking solution, incubated e.g. for two hours, and washed again in physiological saline.

These methods are carried out according to techniques known per se and using known indicators, including staphylococcal protein A. Thus, e.g. $^{125}$I-labeled immunoglobulin can be used in autoradiography, immunoglobulin conjugated with fluorescein for the fluorometric method or with horseradish peroxidase for the enzyme immune method, with the use of o-dianisidine in the presence of hydrogen peroxide, as the substrate for the peroxidase for eliciting a color reaction, in the case of the horseradish peroxidase method, with the colored reaction product being insoluble and remaining immobilized at the site of formation.

All kinds of antibody-containing fluids of a patient, such as serum, plasma, cerebrospinal fluid, colostrum, lymphatic fluid, milk, saliva, urine, stools, etc. can be analyzed with the new kits of the present invention.

The detection of the antigens on the porous support can be made, as said above, with a suitable indicator antibody, or with a component of the complement system, or with a coupled enzyme system which is sensitive to the antigen — antibody reaction. This indicator antibody can also be any antibody which will react specifically with human or animal immunoglobulins, or class specific antibodies which will react only with one desired antibody class such as IgG, IgM, IgA, IgD or IgE or any desired combination of such specific immunoglobulins. IgM antibodies are of special interest as they are characteristic of recent or current infections, IgE of allergy.

The enzymes coupled with the indicator antibodies, when used, may be such as can be localised or quantitated by its formation of a radioactive, luminescent, fluorescent product or a product with characteristic absorbance or reflection spectrum in the visible or outside the visible range, the only requirement being that the detecting reagent or reaction product remains localized at the site of the antigen-antibody complex. When complement is used to detect the bound antigen-antibody complex, it can either itself be labeled in any one of the above ways, or be detected in its turn by a specific anti-complement antibody labeled in any one of the above ways.

The devices of the present invention may be in the form of the solid porous support, e.g. nitrocellulose sheets, as obtained directly after application of the antigens. Such devices may be dried and stored indefinitely at ambient temperature, provided it is maintained in a dehydrated state. The devices of the invention may, however, preferably be in the form as obtained after incubation with proteins for the blocking of residual adsorption capacities, either in one or more steps. Also in this case the support, when dried, can be maintained indefinitely at the said temperature, when protected from humidity, and this form is of particular commercial importance.

In the method of using the devices of the present invention for immunological analysis, the support containing the antigens and/or immunoglobulins, after having been processed with non-specific proteins (second device), is immersed in the liquid to be analyzed, for instance serum or plasma of an animal or human patient or person in routine health care, then is dipped into a diluted solution or suspension of an indicator antibody directed against immunoglobulins of the animal species of the liquid to be analyzed, for instance anti-human immunoglobulins, such as an enzyme-coupled antibody where the enzyme reaction product is insoluble. The last step is the visualization of the bound second antibody, the preferred reaction being the oxidation of 4-chloro-1-naphthol to an insoluble color product. The last steps are sufficiently simple and rapid (the entire operation can be performed within three hours or less) that it is practicable for use in a physician's private practice.

In some cases, thorough drying of the porous support after application of the antigens is advisable or necessary. The support can be preferably air-dried for a minimum of one hour at ambient temperature. Baking is necessary for the case of nucleic acids, and it is only optional for other antigens, without being deleterious. In one particular aspect of the invention, therefore, the kits as obtained by direct application of an antigen, are baked before further processing, especially when nucleic acids antigens are included as part of the program. Baking is conveniently carried out in the temperature range from about 60° to about 120°, preferably at about 80° for a time varying from about 5 minutes to about 12 hours, e.g. for one hour. It is known from the state of the art that denatured nucleic acids bind to nitrocellulose under such conditions. It could not be anticipated that native DNA would also bind under the described conditions, nor that any nucleic acids would remain bound and undegraded under the conditions of the antibody assay.

The basic procedure for carrying out an immuno-assay with the new kits of the invention is as follows: The device is constructed by the application of the antigen to a solid support as described above. There are basically two variants, the "Single dot method", which is used when only one antigen has been applied and samples are to be screened for the presence of the corresponding antibody and the "Multiple dot method", when more than one antigens are applied to test one or more antibodies. In the "Multiple dot method" the arrangement of antigens on the porous support, for instance on a nitrocellulose sheet, can be one dimensional or two dimensional, as has already been pointed out. If the final arrangement is to be a one-dimensional array, the samples are applied as a series of parallel lines and an internal standard series of known concentrations of total immunoglobulins, for example, is applied in the same way.

The residual binding capacity of the support is blocked by soaking the support, for instance the sheet, in buffered saline solution plus the "blocking solution" (e.g. 10% horse serum), for example for 2 hours at 40° C., and then dried. The test support can be stored and shipped in a dry state in this form, or after cutting off individual test strips e.g. perpendicular to the lines of the antigens. The strips can be as thin as is practicable, but should not be more than 3 mm in width. For the actual test, all reagents can be readily stored in a lyophilized form in suitable aliquots, and reconstituted for the test. The serum to be investigated is diluted by a suitable factor in saline containing blocking solution. Dilution factors in the range of 1:100, 1:1000 and 1:10000 cover most uses. The strip is immersed in one of these diluted solutions, for example, in a disposable well insert, as is provided for automated microtiter dilution equipments, such as are used as reservoirs for applying multiple identical samples simultaneously to wells of microtiter plates. The individual wells are usually 10 cm long, 4 mm wide and 1 cm deep. The strips are incubated in this diluted solutions for example between 2 hours and overnight at room temperature with gentle agitation. The excess serum is then washed out with buffered saline, using for example 3 thorough washes. The timing of the washes is not critical. The samples of the indicator antibody are then added. This is usually a 1:1000 dilution of peroxidase coupled goat antihuman IgG (heavy plus light chain) and the treatment continued for up to 2 hours. The dilution is also usually in the same blocking solution. The indicator antibody is then washed out thoroughly by the same procedure, for example 3 times 10 minutes. The indicator antibody is then visualized by an appropriate procedure, such as fluorescence, autoradiography or suitable substrate-for the coupled enzyme. In the case of peroxidase, the substrate might be O-dianisidine or chloronaphthol in the presence of hydrogen peroxide. The color reaction is then allowed to develop, for example from 30 minutes to 2 hours. The individual antibody titers are then read off by selection of the best dilution factor of the original serum, and comparison of the stain intensity with that of the standard series. The color intensity can also be read directly with some densitometric equipment, either by immersing the strip in a medium of suitable refractive index, so that it becomes transparent, and reading the transmission, or by the use of an equipment designed for measuring the reflected intensity. Equipment such as are used for measuring stain intensity on thin layer chromatograms are suitable for this latter purpose, and the same equipment can also measure fluorescence intensity. When the indicator antibody has a fluorescent label or fluorogenic substrate of an enzyme, it can also be quantitated by such equipment.

When the titer is determined with the use of a calibration series with an internal standard of e.g. a normal human serum or a pure human immunoglobulin, the unit is the fraction of total immunoglobulin which is in the form of a specific antibody class, or a simple concentration of that antibody as mass units per unit volume of the original serum. This unit is then of wide utility in comparing sera or plasma from different individuals and even with different assaying systems.

A more specific and preferred way of carrying out the immuno-assays according to the present invention, without limiting its scope, is described below:

A) Single dot method:

(1) Sheet preparation. A rectangular grid is drawn on a sheet of nitrocellulose with less than 4 mm sides, or a nitrocellulose sheet with a 3×3 mm grid already printed on it is used (Millipore Corporation). The sheet is washed with distilled water for 5 minutes and left at room temperature to dry. For the following operations the sheet should be manipulated with blunt tweezers. The washing is not always necessary.

(2) Dotting. When the filter is dry, a small drop of antigen solution is placed into each square. The concentration will vary from antigen to antigen. For complex antigens 0.1–1.0 mg/ml is suitable, for a less complex mixture the concentration can be reduced accordingly. It is often favorable to dry the filter thoroughly at this stage as drying can stabilize the binding. Nucleic acid binding requires 2 hours at 80°. The antigen dotted sheet may be stored dry indefinitely at ambient temperature without any loss of activity. The spots should be as small as possible. For spotting a 20 µl micropipetting device is convenient., alternatively a 5 µl Drummond microdispenser can be used to dot 0.5 µl or Hamilton syringe to dot 0.1 µl. If the antigen is very dilute it is possible to apply successive doses to the same site, taking care that the filter is allowed to dry between each application. The filter is then washed in TBS (This may be 0.15–0.2 M NaCl, 0.01–0.05 M Tris-HCl, pH 7.4–7.8). The individual squares can be cut either while the nitrocellulose is still wet or in a dry state. It can be cut with a scalpel blade while wet or with a scissors together with the backing paper with which it is delivered (this protects it from cracking during cutting). The squares are placed face upward into the well of a 96 well microtiter tray (Costar Inc. Cambridge, Mass.).

(3) Blocking. To each well are added 150 µl blocking solution, which may be bovine serum albumin, whole serum or any combination. (Bovine serum albumin may be 3%, whole serum from rabbit, horse or goat may be 1–10%). It may sometimes be necessary to decomplement the serum by heating the blocking system for 30 minutes at 56°. The blocking is done for 15 minutes to 2 hours at between ambient temperature and 40°. The filters so prepared can also be stored for an indefinite time without loss of activity.

(4) Primary incubation. The blocking solution is aspirated away by the aid of a pipette, e.g. a Pasteur pipette, attached to a suction line, and the antibody test solution (primary antibody) is added. 150 µl per well is easily sufficient, but half as much will suffice. The incubation time will vary from antibody to antibody. For most purposes 2–4 hours are sufficient, but an overnight incubation may give as much as ten times more sensitivity. Antibody dilutions should be made into blocking solutions.

(5) Wash. The test antibody liquid is removed from the wells, e.g. poured out, and the support is washed at least four times, preferably with a TBS solution, and the washing duration may be anything from a few minutes to several hours. (6) Secondary incubation. The support is incubated e.g. for 2 hours in 100–150 µl of horseradish peroxidase conjugated anti-"primary species" immunoglobulin with gentle shaking at room temperature, the "primary species" being that of the antibody to be tested. When, e.g., the primary antibody was raised in mouse, either peroxidase conjugated goat anti-mouse IgG, e.g. from Nordic Laboratories, Tillburg, Netherlands, or rabbit anti-mouse IgG e.g. form DAKO, Copenhagen, Denmark is used. In the case of rabbit or human sera to be analyzed corresponding appropriate secondary (indicator) antibodies, e.g. also from the mentioned Companies can be used. For the detection of specific classes of antibodies, class specific secondary antibodies, such as those specific for IgG, IgA, IgM, IgD, IgE, also obtainable e.g. from Nordic Laboratories cited above, can be used. The concentration of the antibody liquid (to be used preferably in blocking solution, though other diluents dan also be used) vary with the batch of antibody, but 1/1000 of antibody liquid in blocking solution is preferred.

(7) The washing as described under (5) is repeated here for the removal of the second antibody.

(8) Development. 4-Chloro-1-naphthol (Merck), o-dianisidine or 3,3-diaminobenzidine can be used as chromogenic substrates for the peroxidase. 4-Chloro-1-naphthol is prepared as a 3 mg/ml stock solution in methanol, which may be stored for up to one week in the dark and refrigerated. Just before use, it should be diluted with 5–30 volumes of TBS and made 0.01–0.03% in $H_2O_2$ (usually available as a 30% aqueous solution). About 100–150 µl of developing solution is needed per well. Positive color reactions begin to appear after 2 minutes, no further color development is seen after 2 hours. When the reaction is complete, the support is washed with distilled or tap water.

(9) Storage. The nitrocellulose sheets can be mounted with rubber cement as used for photographic mounting, preferably while still moist. Once dry they should be stored in the dark.

B) Multiple dot method: The same steps are followed with the following variations: the antigens are applied in parallel rows on the grid and the blocking is performed on the entire sheet before cutting. The sheet is briefly washed, dried and stored as such. Before use, the sheet is rewetted with TBS and a suitable number of strips is cut off at right angles to the rows of antigens, so that each strip contains one of each of the antigens. The strips are placed into 1–1.5 ml of serum dilutions in troughs of a plastic tray, manufactured by Dynatech (Alexandria, Virginia) "Disposable Reservoir Inserts". These have the same dimensions as microtiter plates and multipipetting devices (e.g. Finpipette Multichannel Pipette). The trays can be used to dilute 8 or 12 samples simultaneously. For the 8 channel insert up to 32 different antigens may be used on a 10 cm long nitrocellulose strip. For washing the liquid is first poured out from the tray and the rest is thrown out. The washing fluid is applied by filling the troughs with a wash bottle. For the secondary antibody, 1–1.5 ml is also used.

C) Quantitation. This is done with an internal standard series of either pure immunoglobulin or with whole serum containing a known amount of total immunoglobulin..The color intensity is matched against that of one of the standards either by eye, or is quantitated with the use of a scanning device. Measurement of the reflectance is done with a thin layer chromatography scanner and gives a precise quantitation with a dynamic range of three decades. The antibody concentration in the original serum is Calculated from the standard curve of reflectance versus amount of immunoglobulin.

The method of anti-body analysis of the present invention shows a high degree of reproducibility of the color reaction when the indicator antibodies named above are used, and when the conditions are otherwise standardized. This color reaction is a quantitative measure of the antibody titer, when a suitable dilution of the serum or plasma is made. Furthermore, the analysis can be quantitated by adopting an internal standard series of human immunoglobulin concentrations, for instance by applying, standardized amounts of pure human IgG to the micro-porous support before the non-specific sites are blocked by the described procedure. This will give a standard color series after the test and will automatically compensate for any variation due to the unknown serum or plasma or other cause. One source of variation is that individual sera give different background binding reactions either to the proteins used for blocking the non-specific binding sites, or with non-specific sites on the microporous sheet which evade the blocking procedure. This background varies with individual sere for unknown reasons, and might itself be of a diagnostic value. However, the presence of the applied antigens in the form of spots permits a very sensitive direct visual determination of the presence or absence of antibody.

Such small differences are hard to see visually in conventional enzyme-coupled antibody assays which depend on the use of microtiter plates, for example, where one would be comparing very similar samples in different wells. It is quite unexpected that because of the physical juxtaposition of the antigen on its own background on the microporous sheet, significant differences are detectable which would otherwise be impossible to determine, either visually or spectrophotometrically.

The above-mentioned quantitative color reaction and use of internal standards permits the use of instrumentation for the quantitative determination of the titers of individual antibodies. This can be done with any common densitometer as is used for the analysis electropherograms or chromatograms. The optical density can be determined by rendering the microporous sheet transparent by immersing in a solvent of suitable refractive index and which will not solubilize either the colored reaction product or the microporous sheet. It is well known from the use in scintillation counting of radioactivity that toluene will render nitrocellulose transparent in this way. In practice, neither toluene nor xylene nor glycerol-water mixture will solubilize the color of the o-dianisidine oxidation product, while rendering the support transparent. Furthermore, a quantitative response to the antibody titer is obtained with the antibody within a thousand-fold range below the concentration which will saturate the antigen. A detailed dilution series is therefore not required, which makes the invention eminently suitable for a routine use.

In some diseases, especially chronic infections, it is well known that there is a large increase in the concentration of a heterogeneous population of antibodies of a given class, but of unknown reactivity. These are called polyclonal gammopathy. Testing of serum or plasma from such a patient with a large number of randomly selected antigens will facilitate the diagnosis of such disease.

For example, the serum of a patient with infectious mononucleosis shows unexpectedly high antibody titers against 10 out of the 17 antigens used, including against the control antigens (see Example 3). Particularly high is the antibody titer against measles virus, which is antigenically unrelated, and is not previously described as having any connection with the etiology of infectious mononucleosis, which is due to infection with a totally unrelated virus. This titer is even higher than in the serum which is commercially available as a measles positive control human serum. The discovery of this unexpected high titer against measles virus will be useful in diagnosis of infectious mononucleosis. Furthermore, the detailed antibody profile will be an important new tool for the diagnosis of disease obtained with polyclonal gammopathy.

The devices described above according to the inventions are not limited to the use for antibody analysis: they can serve any objective of analytical character in biochemistry and immunology involving naturally occurring macromolecular organic substances of animal or vegetable origin, such as naturally occurring or artificially produced proteins, naturally occurring protein conjugates, such as glycoproteins, lipoproteins or protein-nucleic acid complexes, insofar as they can be applied in the said manner to porous solid supports. Immunoglobulins will also bind to the said supports, and this is why in the above described test the non-specific background binding must be eliminated before carrying out the immunological assay. Ribonucleic acid and desoxyribonucleic acids can also be used in assays with the new kits of the invention, the latter being particularly of importance when, included in the programme for testing auto-immune disease.

The devices according to the present invention are also suitable for detecting rheumatoid factor and circulating immune complex. Such immunoglobulins or antigen-immunoglobulin complexes are often encountered in sera of patients with chronic inflammatory conditions, especially with connective tissue diseases. In the case of rheumatoid factor, IgG of an animal species, e.g. rabbit, are applied to a porous support, e.g. nitrocellulose, incubated with a blocking solution as described above, and then with the serum, e.g. human serum to be analyzed. The rheumatoid factor will bind to the IgG on the kit, and the complex so formed and the bound rheumatoid factor can be recognized by an indicator antibody directed against the species of the serum to be analyzed, and is for instance anti-human antibody, e.g. rabbit-anti-human. The indicator antibody is coupled, as usual, to an enzyme, forming a colored reaction product with a suitable substrate. If set up to detect rheumatoid factor which is not species specific, such as human anti-rabbit rheumatoid factor, one would have expected that the non-species specific class of antibodies would be competed out effectively by the large excess of IgG of other species, such as horse, present in the blocking solution. This, very surprisingly does not happen.

In the case of immune-complex assays the protein Clq retains its ability to bind specifically antigen-antibody complexes even when deposited on the nitrocellulose. This is very surprising in view of the well-known instability of this protein. It remains stable at ambient temperature in a dry state on the support.

The group of antigens which can be used with the new kits of the invention and for carrying out e.g. immunological assays is very extensive and includes e.g. human biopsy material, mammalian tissue or cells, bodily fluids, mycoplasma, metazoan parasites, fungi, bacteria, protozoa, viruses, or preparations derived from any of these. Apart from the antigens described in the illustrative Examples the following should be mentioned as being suitable to be used according to the invention: Viruses or antigens prepared form them: influenza strains, including A, $A_1$, $A_2$, B, C, parainfluenza strains 1, 2 or 3, Lymphocytic choriomeningitis virus, Mumps, Q fever Rickettsia, Rabies, Respiratory syncytial virus, Rotavirus, Rubella, Adenovirus, Eppstein Barr virus, Brucella, Hepatitis B, Cocksackie B1–B6, A9, Polio 1, 2 or 3, Reo, Echo 1–33; Fungal antigens: *Histoplasmosa capsulatum, Coecidioides immitis, Blastomyces dermatitidis, Aspergillus fumigatus, flavus or carnea;* Parasitic antigens: *Entemeba histolytica, Trypanosoma cruzi, Echinococcus granulosis, Schistosoma mansoni;* Bacterial antigens: *Spirochete reiter, Treponema pallidum, Escherichia coli, Leptospira, Listeria, Salmonella, Shigella, Staphylococci, Streptococci, Legionella pneumophila;* Autoantigens: Nuclear RNP, complement fractions, Human serum proteins, Rheumatoid factor, Insulin, Insulin receptor, Thyroid stimulating hormone receptor, Acetylcholine receptor and other hormones or receptors; moreover all allergens, such as those of gramineae, e.g. *Dactylis glomerata, Festuca elatior, Lolium perenne, Phleum pratense, Poa pratensis, Agristis stolonifera, Secale cereale,* of herbs, e.g. *Artemisia vulgaris, Chrysanthemum leucanthemum, Chenopodium album, Taraxum vulgare, Solidago virgaurea, Ambrosia trifida,* of trees, e.g. *Olea europea, Juglans californica, ulmus americana, Corylus aveliana, Platanus accrifolia,* fungi, e.g. *Penicillium notatum, Cladosporium herbarum, Aspergillus fumigatus,* animals epithelia, e.g. of cats, horses, oxen, dogs or guinea pigs, of food-stuffs, e.g. milk, wheat, almonds, crabs, crevettes, of mites, of dust, of insects, e.g. of bees or wasps and of medicaments, e.g. penicillin G, penicillin V, synacthen, steroids, etc.

Immunological procedures will also be of extreme importance in the detection and monitoring of specific drugs. Such tests based on the use of monoclonal antibodies, for example, during the course of treatment of a disease, consist in applying the specific antibodies to a porous support and to detect and quantirate specific antigens by the inverse of the immuno-assay procedures principally described above. The property of complement proteins to bind specifically to antigen-antibody complexes can then be used directly or indirectly to visualize and quantitate the specific antigens, such as drugs or other pharmacological reagents, or hormones, or any desired combination of such antigens, in a kit such as is described here. The present invention therefore includes also an immunological method for analyzing antigens of any kind, for instance also drugs and hormones, by applying corresponding specific or monoclonal antibodies to the solid support according to the invention, and detecting the antigen-antibody complexes, e.g. by complement, e.g. complement Clq, or by enzyme reactions coupled to the antibody-antigen interaction. The monitoring of specific drugs and hormones in biological fluids for diagnostic purposes has been facilitated in recent years by the use of the so-called "homogeneous antibody assay systems" under the trademark of EMIT of the Syva Corporation, Calif. Such assays dispense with the necessity of extensive washing needed in other immuno-assay systems, and are consequently both simpler in operation and more rapid. The homogeneous antibody assay depends on the use of a specific antibody against the drug or hormone in question, and an adduct between the drug or hormone molecule and a signalling molecule. The signalling molecule adduct is an adduct for which a measurable signal is supressed when it is bound to the specific antibody. When the latter binding is inhibited by the presence of the drug or hormone in question, a positive signal results which is related to the concentration of the drug or hormone in a biological fluid. The signalling molecule may be an indicator enzyme itself, or a substrate, co-factor or prosthetic group for an indicator enzyme or coupled series of enzymes resulting in a measurable signal.

In a recent publication, entitled "Flavin Adenine Dinucleotide as a Label in Homogeneous Colorimetric Immuno-assays" by D. L. Morris, P. B. Ellis, R. J. Carrico, F. M. Yeager, H. R. Schroeder, J. P. Albarella, R. C. Bogulaski, W. E. Hornby and R. Dawson, in the Journal "Analytical Chemistry", Volume 53, pages 658–665 (1981), a method is described where a molecule of the analyte is coupled covalently to flavin adenine dinucleotide, which is a prosthetic group for the enzyme glucose oxidase. When bound to a specific antibody, the flavin adenine nucleotide adduct with the analyte is unable to activate the glucose oxidase. When the adduct is prevented from binding to the specific antibody by the presence of the analyte, the glucose oxidase is activated, and the activation is related to the quantity of the unknown drug or hormone. The activated glucose oxidase produces $H_2O_2$ as a reaction product, and the $H_2O_2$ is a substrate for peroxidase, which can then be used together with a chromogenic substrate to yield a color reaction.

Homogeneous antibody assay systems can be readily adapted to use on a solid support according to the method of the present invention. The specific antibody and the macromolecular components of the signalling system, for example glucose oxidase and horse radish peroxidase, may be mounted by direct application on the solid porous support in any desired geometry, preferably in the same location. The coupled enzyme reactions will then benefit from their physical coincidence. According to the methods of the present invention, multiple antibodies and indicator enzymes of a signalling system can be mounted on the same support to facilitate the assay of multiple antigens simultaneously. This approach will be of great utility, for example, in drug abuse assay kits and in specific bacterial antigen identification kits. The present invention, as far as it is directed e.g. to the manufacture of the new devices to be used for analytical purposes in the field of immunology, and to the use of such devices for immuno-assay as described, encompasses also the single steps of such processes.

Furthermore, the invention relates to kits comprising besides the described devices in the form of the solid supports also trays and other hardware suitable for processing the solid supports in the assays, as well as prepared reagents in dry form, such as predetermined amounts of carrier serum, indicator antibodies, peroxidase substrates, etc. Such kits are e.g. in the form of outfits including the devices of the invention, for instance in the form of nitrocellulose sheets or strips, and any of the above mentioned accessories. In particular, trays may take the form of multicavity plastic trays, and the dried reagents are a lyophilized mixture of indicator antibodies, salts, buffer, carrier serum or proteins, and the color reagents for the indicator enzymes are pre-weighed aliquots of chromogenic substrate, e.g. 4-chloro-1-naphthol, salts, buffer and ampoules containing pre-measured quantities of liquid substrates, e.g. hydrogen peroxide.

The invention especially includes a kit and/or device comprising an indicator antibody radioactively labelled where detection and quantitation is to be carried out by counting or autoradiography; or is conjugated with a fluorescent indicator Where detection and quantitation is to be carried out by fluorimetry or is conjugated with an enzyme capable of giving a color reaction with a suitable substrate where detection and quantitation is to be carried out by densitometry or visually; or comprises a detection and quantitation system based on complement protein binding to antigen-antibody complexes, where the complement itself is labelled by one of the above three methods or by means of a further specific anti-complement antibody, also labelled by any one of the above three methods.

Furthermore the invention is particularly directed also to a kit and/or device, in which a) a solid support contains an array of one or more specific antibodies and reagents for a signalling system whereby the antigen-antibody reaction results in a measurable signal, the signalling system comprising a substrate, cofactor or prosthetic group for an indicator enzyme or coupled series of enzymes, or a covalent adduct between antigen and the signalling molecule. The enzyme or coupled enzyme system can be applied together with the specific antibody or separately from it to the solid support; however, it need not be applied to the support at all, but it may be used in solution, b) the array on the solid support contains immunoglobulins of human or animal origin, or fragments thereof, for the detection and quantitation of rheumatoid factor, c) the array on the solid support contains complement protein for detection and quantitation of circulating antigen-antibody complexes known as circulating immune complexes.

The invention furthermore relates to the use of all the kits and devices above described, especially for the detection and quantitation of specific antigens or specific antibodies or both, by immuno-assay methods for the diagnosis, surveillance and prognosis of diseases in humans and animals; for the detection and quantitation of monoclonal and other antibodies or antigens in research and development and for the detection and quantitation of unknown antigens applied to solid supports with immuno-assay methods using known antibodies.

The following Examples illustrate the invention. The temperatures are indicated in degrees centigrades.

Example 1: Variation of dot-size

Total human serum is applied directly to a sheet of Millipore (0.45 μm pore size) and the IgG in it stained by peroxidase— coupled goat — anti-human IgG. The volume applied is varied in order to determine the minimum feasible size of microdot. A normal human serum is diluted 1:1000 by volume in TBS (0.15M NACl, 0.02M Tris-HCl, pH 7.4) containing 2% bovine serum albumin. Aliquots of this solution are then spotted directly with a microsyringe (preferably a Hamilton microsyringe) graduated in 0.1 μl steps, on to a strip of Millipore 3 mm× 100 mm. The sheet is then dried, soaked in TBS containing 10% (v/v) horse serum and incubated at 40° C. for two hours to block the non specific protein binding sites on the Millipore sheet. The sheet is washed with TBS and then soaked in 1 ml of peroxidase coupled goat anti-human IgG (Nordic Laboratories, Tilburg, Netherlands) dissolved according to the manufacturer's specifications in distilled water, and diluted 1:1000 in TBS containing 10% horse serum. The treatments are performed in the well of a disposable 8 trough reservoir insert (Dynatech Laboratories, Alexandria, Virginia, USA). The incubation with the peroxidase coupled antibody is effected at room temperature during two hours with gentle agitation. The excess antibody is removed by thorough washing with TBS. Finally, the peroxidase substrate mixture is made up with 5 ml TBS, 1μl 30% $H_2O_2$ in water, 10μl o-dianisidine (1% w/v in methanol) and 1 ml of this solution is added to the trough. The reaction is then allowed to proceed for 2 hours in the dark. The excess reagents are washed out with de-ionized water, the strip air-dried at room temperature, and the size of the spots measured with Vernier calipers. The following results are obtained:

| Volume of serum | Diameter of spot |
| --- | --- |
| 0.8 μl | 1.5 mm |
| 0.6 μl | 1.3 mm |
| 0.4 μl | 1.0 mm |
| 0.2 μl | 0.6 mm |
| 0.1 μl | 0.3 mm |

The diameter of the microdot is linear with respect to the volume applied when this is in the range 0–0.2 μl. It falls off from linearity at higher volumes, probably due to adsorption at the point of application. Furthermore, if Millipore sheets with a grid are used, the ink is sufficiently hydrophobic that the liquid does not spread beyond the printed squares. The intrinsic resolving power of the microdot system is clearly well below the size of the smallest volume that can be applied with common pipetting devices, namely <0.3 mm. A standard 100 mm length strip, fitting in the well of "trough reservoir insert", as used here, could contain 300 individual antigens spotted in a one-dimensional array. If a two dimensional array of dots is used, a ten cm square can contain up to $10^5$ individual tests.

Example 2: Epidemiological screening of influenza virus antibodies.

A series of standard influenza virus strains are obtained from Flow Laboratories (Rockville, Maryland, USA), as used for standard hemagglutination tests. The viral antigen suspensions are spotted in the 3 mm× 3 mm marked squares of a sheet of Millipore (pore size 0.45 μm) as obtainable from the manufacturers with a grid printed on it. The applied samples are 0.5 μl of undiluted material. An influenza vaccine (Sandoz "Sandovac") is also spotted on. The samples are spotted on in linear arrays, each line containing only spots of one and the same strain, in such a way that after treatment the sheets can be cut into strips, each strip containing one dot of the complete set of antigens. The sheet is then treated as described in Example 1 for the blocking of the non-specific binding sites with horse serum, and dried. The test device when kept dry, can be stored indefinitely at ambient temperature without loss of antigenicity. Serum is taken from an individual who has been immunized with the above mentioned vaccine approximately three weeks before. A series of dilutions of this serum are made in TBS 10% horse serum, starting at 100-fold dilution and then in 5-fold steps. A series of strips are cut out from the test device as described above.

The strips are soaked overnight at ambient temperature in the dilutions of the serum with gentle agitation, and then washed thoroughly with TBS. The bound antibody is then stained with the indicator peroxidase coupled goat-anti-human IgG exactly as described in Example 1. The titer of the antibody is scored by an end-point-procedure as the highest dilution at which the stain is still visible, and the titer expressed as the reciprocal of this dilution factor. The following results are obtained:

| Antigen used in test | Antibody titer |
| --- | --- |
| Sandovac vaccine (mixture) | |
| A/Brazil/11/78 </br> A/Bankok/1/79 </br> A/Singapore/222/79 | 625,000 |
| Flow hemagglutination test antigens | |
| A/PR-8/34 | 2,500 |
| A-1/FM-1/47 | 12,500 |
| A-2/Hong Kong/68 | <100 |
| A-2/England/42/72 | <100 |
| A-2/Japan/170/62 | <100 |
| B/Lee/40 | 500 |
| B/Mass/3/66 | 500 |
| Negative virus control | <100 |

This shows that the serum has an extremely high titer of antibodies against the antigen with which the individual had been vaccinated, varying but significant titers against some historical influenza strains, and no detectable titer against the control antigen preparation which has no virus. Thus, all influenza strains can easily be titered against a serum of an individual in one single operation. The method is also very sensitive: endpoint at c. $10^6$-fold dilution for high titer antibodies; and requires very little serum: 10 μl in 1 ml of medium for the lowest dilution. This method is also superior to the conventional hemagglutination inhibition tests or complement fixation tests, where individual assay procedures are required for each antigen. The strip also gives a permanent record of the results, and can be stored indefinitely.

Example 3: A device constructed from 10 pre-existing immunediagnostic kits

The device is constructed by spotting commercially available antigens as in Example 2. The following antigens are used with dilution factor indicated being sufficient to give the maximum response. The antigens are all diluted in TBS.

| Antigen description | Dilution used |
| --- | --- |
| Behring: | |
| Toxoplasma from fluorescent antibody test kit | Undiluted |
| Measles hemagglutination inhibition test | 1/25 |
| Ornithosis complement fixation test | Undiluted |
| Herpes Simplex type 1 complement fixation test | 1/25 |
| Mycoplasma pneumoniae complement fixation test | 1/5 |
| Tick-borne encephalitis virus complement fixation test | Undiluted |
| Varicella Zoster virus complement fixation test | 1/5 |
| Flow: | |
| Adenovirus type 4 virus complement fixation test | 1/5 |
| Cytomegalovirus (Ad 169) virus complement fixation test | 1/5 |
| Sandoz: | |
| Sandovac influenza vaccine | Undiluted |

These examples are selected on the basis of the availability of positive control human sera as part of the diagnostic kit. However, as is clear from the first Example the number of antigens per test can be increased, if desired, to a much larger number.

The samples and, where available, negative control antigens, are spotted on to a sheet of Millipore with a grid printed on it, as in Example 2, and the nonspecific sites blocked with horse serum, dried and stored as in the previous examples. Individual strips are cut from the sheet as in Example 2, and tested with the positive and negative control antisera, as provided with the kits listed in the preceding table. The sera are all diluted 1:100 in the TBS — 10% horse serum, and the relevant test strips are processed as in Example 2. In this series, the results are scored as positive or negative, for each antigen against each serum. This is summarized in the following table.

| | Test antisera | | | | | | | | | | | | |
|---|---|---|---|---|---|---|---|---|---|---|---|---|---|
| Test antigens | Mono-nucleosis | Mono-nucleosis control | Toxo-plasma | Toxo-plasma control | Meas-les | Meas-les control | Orni-thosis | Herpes simplex | Myco-plasma | Adeno-virus | Cyto-mega-lovirus | Tick-borne ence-phalitis | Vari-cella zoster |
| Toxoplasma | − | − | ⊕ | − | − | − | − | − | − | − | − | − | − |
| Measles | + | − | + | − | ⊕ | − | + | − | − | − | + | − | − |
| Ornithosis | + | − | − | − | − | − | ⊕ | − | − | − | − | − | − |
| Ornithosis control | + | − | − | − | − | − | − | − | − | − | − | − | − |
| Herpes simplex | + | + | − | + | + | − | + | ⊕ | + | + | + | + | + |
| Herpes simplex control | + | − | − | − | − | − | − | − | − | − | − | − | − |
| Mycoplasma | + | − | − | − | − | − | + | + | ⊕ | + | − | − | − |
| Mycoplasma control | − | − | − | − | − | − | − | − | − | − | − | − | − |
| Adenovirus | − | + | − | + | + | − | + | + | + | ⊕ | + | + | + |
| Cytomegalovirus | + | + | − | − | + | − | + | + | + | − | ⊕ | + | − |
| Cytomegalovirus control | − | − | − | − | − | − | − | − | − | − | − | − | − |
| Tick-borne encephalitis | − | − | − | − | − | − | − | − | − | − | − | ⊕ | − |
| Tick-borne encephalitis control | − | − | − | − | − | − | − | − | − | − | − | − | − |
| Varicella zoster | + | + | − | + | + | − | + | + | + | + | + | + | ⊕ |
| Varicella zoster control | − | − | − | − | − | − | − | − | − | − | − | − | − |
| Influenza | + | + | + | + | + | − | + | + | + | + | + | + | + |
| Influenza control | + | − | − | − | + | − | − | − | − | − | + | − | − |

In every case, the spot is positive for the combination of a test antigen with the corresponding test antiserum, as emphasized by the circles.

The negative control sera are all negative for the antigen for which they are provided in the purchased kits, although each may be positive for a variety of other antigens. The negative control antigens are also negative with the sera for which they are provided, although occasionally other sera may have antibodies directed against these preparations. The procedure of the present invention therefore attains the same specificity as with the kits from which it was constructed.

Many of these tests are for antibodies against endemic viruses such as Herpes simplex, Varicella zoster or adenovirus. It is therefore not surprising to find such endemic antibodies in many sera which were not specifically supplied as being positive for these antigens. In practice, the complete absence of such an antibody will be indicative of a flaw in the immune defense system of the individual, and suggests a high susceptibility to infection by the agent in question. In practice, as with many of the commonly used serological procedures, only a changing titer is diagnostic of actual infection. The mononucleosis serum has a range of antibodies against a wide variety of apparently unrelated antigens. The titer of antibodies against measles virus is especially high. This appearance of a wide spectrum of apparently irrelevant antibodies, including some against some of the negative control antigen preparations, is indicative of a polyclonal gammopathy and is diagnostic of infectious mononucleosis.

Besides the infectious mononucleosis serum, several other sera give antibodies against the influenza control antigen. This is included to illustrate the worst case of an impure antigen. The influenza antigen is a highly purified virus preparation, as used in humans as vaccine, while the control antigen is a much less pure preparation still containing egg proteins as impurities. In any case, the titer of antibodies against this control are always lower than the titer against the viral antigen. The presence of such antibodies against impurities indicates that the patient from which the serum was taken was allergic to impurities in the commonly used vaccine preparation. Alternatively, it might indicate that the person had an allergy to egg. In practice, the monitoring of such antibodies routinely will be useful to control against allergies in vaccines, the environment and foodstuffs.

Allergies are usually associated with the presence of circulating antibodies of the IgE type. As described here, the assay with indicator antibodies of peroxidase coupled goat anti-human IgG also detects IgM and IgE antibodies, since the goat antibody used reacts with both H and L chains. More specific tests can be constructed using antibodies which are specific for IgG or IgM, or IgE for example.

Example 4: Analysis of antibodies in the sera of patients with auto-immune and other diseases This device is constructed with the same antigens as used in Example 3, but with the addition of antigens which are indicative of auto-immune disease. Pure and denattired nucleic acids, as described below, and subcellular fractions derived from Hela cells, which can be taken as a typical. non-differentiated human cell line, and which is readily cultivated in quantity, are used. Actin and myosin are also used as antigens (rabbit: from Sigma).

Salmon sperm DNA (Serra, Heidelberg) is denatured by heating at 100° C. for 2 minutes in the presence of 1M glyoxal, followed by fast cooling.

*Escherichia coli* ribosomal RNA is prepared from the large ribosomal subunit by well-known procedures (Gordon & Ramjoué, Analytical Biochemistry 83, 763–766 (1977)).

Hela cells are cultivated and the subcellular fractions (nuclei, mitochondria, nucleoli, polysomes and cytosol fractions) prepared from them by known procedures (Penman, S. J. Mol. Biol. 17, 117–125 (1966)).

Aliquots of 0.5 µl of all the antigens mentioned with protein concentrations in the range 1–10 mg/ml are spotted on Millipore sheets as described in Example 3, in two steps as follows:

1) fixation of the nucleic acids by direct spotting and baking of the sheet for 2 hours at 80° C., a procedure already known to cause an irreversible fixation of RNA and denatured DNA to nitrocellulose (P.S. Thomas, Proc. Nat. Acad. Sci. US 77, 5201–5205 (1980)). It was not previously known that native DNA can also be bound in this manner.

2) The spotting on the so treated Millipore sheet of the rest of all other mentioned proteins, cells or sub-cellular fractions.

The devices are then prepared as described in the preceding Examples and strips cut off to test the individual sera of patients suffering from auto-immune diseases and some control patient sera. The sera are tested at 1/100-, 1/1000- and 1/10 000-fold dilutions in TBS-10%-horse serum and processed as in the preceding Examples. In addition the devices contain 0.5µl spots of a normal human serum, as an internal standard of IgG in the test. These are at 1/1000, 1/2000, 1/4000 and 1/8000 dilutions in TBS, 1 mg/ml bovine serum albumin.

The diseases are diagnosed according to the criteria of the American Rheumatological Association. The results obtained are summarized in the following Table

| Test | Normal | | SLE | | | | | | RA | | | | | | |
|---|---|---|---|---|---|---|---|---|---|---|---|---|---|---|---|
| | 15 | 17 | 2 | 5 | 7 | 8 | 9 | 1 | 10 | 12 | 14 | 16 | 18 | 19 | 20 |
| Native DNA | | | | | 5 | | | | | | | | | | |
| Denatured DNA | | | | | | | | | | | | | | | |
| RNA | | | | | | | | | | | | | | | |
| Hela cells | | | 5 | 5 | 5 | 12.5 | <1 | <1 | | | | | | 1 | <1 |
| Mitochondria | | | 5 | | | | | | 50 | | | | | | |
| Nuclei | | | 5 | 12.5 | 5 | 12.5 | | | | | <1 | | | 1 | 1 |
| Nucleoli | | | 5 | | <1 | | | | | | <1 | | | | |
| Cytosol | | | 5 | | <1 | | | | | | | | | | |
| Ribosomes | | | 5 | | | | | | | | | | | | |
| Myosin | | 2 | | | <1 | | | | | 1 | | | | | |
| Toxoplasma | | <1 | <1 | <1 | <1 | | <1 | <1 | <1 | | | <1 | <1 | | <1 |
| Measles | <1 | <1 | <1 | <1 | <1 | <1 | <1 | 5 | <1 | 1 | <1 | 5 | <1 | 1 | 1 |
| Ornithosis | | | | | | <1 | | | | | | | | | |
| Herpes | <1 | 12.5 | 2.5 | | | 5 | 1 | 12.5 | <1 | 10 | 1 | 10 | | 2 | 5 |
| Myco plasma | 1 | 1 | 1 | | | | | | | | | | | | 1 |
| Adenovirus | 10 | 5 | 1 | <1 | 1 | 1 | 1 | | | 2 | 1 | <1 | 5 | 1 | 5 |
| Cytomegalovirus | 5 | | | | 1 | <1 | 1 | | | | | | | 5 | |
| Varicella | 2 | 10 | 1 | <1 | 2 | 1 | 1 | 1 | 12.5 | | 1 | 1 | 5 | 1 | 1 |
| Influenza | 10 | 10 | 1 | 5 | 5 | 12.5 | 12.5 | 2 | 12.5 | 25 | 5 | 10 | 10 | 10 | 1 |
| Influenza control | | | | | | | | | 1 | | | | | | |

| Test | SLE + RA 6 | MCTD 11 | MS 3 | ICD 4 | AE 13 |
|---|---|---|---|---|---|
| Native DNA | | | | | |
| Denatured DNA | | | | | |
| RNA | | | | | |
| Hela cells | | | | | |
| Mitochondria | | | | | |
| Nuclei | | | | | |
| Nucleoli | | >500 | | | |
| Cytosol | <1 | >500 | | | |
| Ribosomes | | >500 | | | |
| Myosin | | >500 | | | |
| Toxoplasma | | 1 | | | |
| Measles | | | <1 | | |
| Ornithosis | <1 | <1 | <1 | <1 | <1 |
| Herpes | 5 | | 12.5 | <1 | |
| Myco plasma | | <1 | | <1 | <1 |
| Adenovirus | <1 | 1 | 5 | <1 | 25 |
| Cytomegalovirus | 2 | <1 | | | |
| Varicella | 5 | 12.5 | 1 | 2 | 10 |
| Influenza | 10 | 2.5 | 5 | 2 | 2 |
| Influenza control | | 1 | | | <1 |

In this Table antibody titers are from sera of normal individuals or such suffering from the indicated diseases. Sera are numbered 1–20. Titers are expressed as the fraction of total immunoglobulin as specific antibody X $10^{-5}$. Where no significant antibody is detected there is no entry. Where there is significant antibody, but outside of the range of the standards, the result is given as <1 or >500.

SLE = systemic lupus erythematosus, RA = rheumatoid arthritis,

MCTD = mixed connective tissue disease, MS = multiple sclerosis,

ICD = immune complex disease, AE = angioneurotic edema.

A significant number of auto-antibodies are found in the auto-immune sera: in one case specific antibodies against native DNA, and not reactive with denatured DNA, are present, and in others, against whole cells, organelles, etc., from which it is apparent that the test is sensitive for a much wider spectrum of antigens than only proteins. In a collection of twohundred individuals SLE sera, titers of antinative DNA and anti-denatured DNA are found to vary widely amongst different individuals, and independently of each other. This shows that the assay is specific. In some cases it is possible that auto-immune antibodies are no longer present because these sera are from patients already under treatment. As in other circumstances, described previously, antibodies directed against egg protein are occasionally detected in the influenza virus controls.

This assay system has the following advantages over pre-existing methodology for the diagnosis of auto-immune diseases: all interesting antibodies can be measured in one procedure rather than in separate ones. Specific antibodies against subcellular compartments are normally determined by fluorescence microscopy. This is tedious, subjective, and timeconsuming, while the present procedure is simple and can be automatically quantitated. Rabbit actin and myosin are included because of their commercial availability. It is clear that the method can detect antibodies against these proteins. However, their substitution by the corresponding human proteins is possible, as well as by human collagen, for the diagnosis of autoimmune diseases. Furthermore, a variety of differentiated cell types making specialized proteins can also be included, as well as the undifferentiated Hela used here. This kit has the additional advantage that it can be used for the monitoring of patients sera during the course of treatment of autoimmune disease with immunosuppressive agents. One can then monitor the disappearance of pathological anti-bodies, and regulate the treatment so as to avoid the suppression of the benign antibodies which are endemic, and thus avoid totally compromising the immune system of the patient.

Example 5: The limits of sensitivity of the multiparameter antibody analysis

A standard series of dilutions of pure human IgG are spotted on to Millipore sheets as in Example 1. The sheets are then processed in exactly the same way as in Example 2, using a 1/100 dilution of the same serum as was used in Example 2.

The reflectance of the spots is quantitated using a Thin Layer Chromatogram Scanner, manufactured by the Company "Camag", Muttenz, Switzerland. The following results are obtained.

| Amount of IgG in dot (ng) | Reflectance (arbitrary units) |
| --- | --- |
| 50 | 54 |
| 23.3 | 49 |
| 10.8 | 41.8 |
| 5 | 37 |
| 2.33 | 22 |
| 1.08 | 14 |
| 0.5 | 10 |
| 0.23 | 7 |

It can be seen from the table that the reflectance measurement yields quantitation of the antibody over a dynamic range of greater than three decades of amount of bound antibody, and less than 0.5 ng of bound antibody can be detected.

Example 6: Comparison of different peroxidase substrates

The antibody analysis of Example 5 is repeated in duplicate: In one case the exact procedure of Example 5 is followed, in the second case the following modification is carried out: 5 ml TBS, 10 ul $H_2O_2$ (30% w/w in water) and 0.3 ml of 4-chloro-1-naphthol 0.3% w/v (Merck) in methanol, instead of o-dianisidine. The sensitivity of the staining is identical, but the o-dianisidine gives a slightly higher background than the 4-chloro-1-naphthol. Diaminobenzidine can also be used. 4-Chloro-1-naphthol is to be preferred for commercial use, because it is not known to be a carcinogen.

Example 7: Screening of monoclonal antibodies against neuronal membrane fractions In the preparation of hybridoma cell lines one has to screen large numbers of clones possibly making the specific antibody of interest. If it is desired to screen each Clone for antibodies against multiple separate antigens, the methodology of the preceding Examples can be used with little modification. If it is desired to screen for antibodies against a single antigen, the following procedure can be used: A sheet of Millipore is marked into squares of 4 mm or less, or the Millipore sheets commercially available as used in the preceding Examples with squares already printed on are used. It is sometimes an advantage to pre-wash the Millipore sheet in distilled water. Rat brain synaptosomal plasma membrane (Jones, D. H., Matus, A. I., Biochem. Biophys. Acta 356, 276–287 (1974) is used as antigen at a concentration in the range of 0.1–1 mg/ml of protein. Volumes of 0.5 µl of these antigen preparation are spotted on to the Millipore sheet as described e.g. in Example 2. If necessary, the local concentration can be raised by repeated application to the same spot, with drying between different applications. The sheet is then washed with TBS and, if desired, treated with a blocking solution of horse serum as in the preceding Examples, dried and stored. The individual squares are cut out and placed in the wells of a Costar tray (Cambridge Mass. U.S.A.). Each well is treated with 150 µl of 3% bovine serum albumin, 1% normal goat serum in TBS for about 15 minutes with shaking at ambient temperature. Alternatively, if the Millipore sheet was treated with the blocking solution the wells can be coated separately. The coated trays and filters can also be stored dry as such.

Mice are immunized with the rat brain synaptosomal membrane preparation, the spleens removed, hybridized with myeloma cells, and distributed in 200 wells in selective medium to permit the growth of hybridomas, by known procedures [G. Köhler, C. Milstein,, Nature 256, 495–497 (1975)].

After 10 days, aliquots of the supernatant from the wells are placed in the Costar plate wells containing the squares (75–150 ul per well) or dilutions therefrom into blocking solutions, and the antibody binding reaction permitted to continue for between two hours and overnight, depending on the activity of the antibody. The medium is then removed and the excess antibody removed by extensive washing with TBS. The bound immunoglobulin is then specifically stained with peroxidase coupled goat-anti-mouse IgG, using the same procedure as in the preceding Examples. Out of the 480 wells 170 positives are detected.

This procedure can be used for the preparation of kits for the screening of hybridomas against any desired antigens or mixtures of antigens. It has the advantage of permitting the easier handling and storage of the antigen if it is immobilized on sheets or squares rather than on conventional plastic dishes, it requires less antigen than if the entire well of the Costar dish is coated with the antigen, and it permits the direct comparison of the antibody binding to the antigen compared with the background staining on the Millipore, thus permitting highly sensitive discrimantion and elimination of false positive due to high background reactions.

Example 8: The tissue distribution of rat brain antigen recognised by a monoclonal antibody (MIT-23).

The monoclonal antibody is obtained as in Example 7. This monoclonal antibody is used to assay for MIT-23 antigen in crude homogenates from various rat tissues. In each case the homogenate is dotted at 1.0 mg/ml. The tissues are: liver, cerebellum, forebrain, kidney, thymus, striated muscle, heart muscle. The antigen MIT 23 is present both in cerebellum and forebrain, but not in the other tissues tested. Experiments in which the antigen concentration in the dot is progressively reduced show that MIT-23 can be detected in a cerebellar homogenate at 50 µg/ml but not at 10 µg/ml, suggesting that the negative members of the tissue panel have less than 5% of the MIT found in cerebellum.

Example 9: Determination of rheumatoid factor and circulating immune complex in the serum of humans or mice with autoimmune disease Rheumatoid factor is defined as an immunoglobulin found in serum which will bind to IgG, including IgG of other species. Circulating immune complex is an endogenous antigen-antibody complex found in circulation in certain disorders. Both of these are frequently measured as part of the diagnosis of connective tissue disease. Rabbit IgG (Nordic) is used as the test for rheumatoid factor, human Clq as the test for immune-complex. The Clq complement fraction will specifically recognize antigen antibody complexes.

The rabbit IgG and Clq are dissolved at 1 mg/ml in TBS and 0.5 ul spots are applied to nitrocellulose. The sheets are then blocked with TBS-10% horse serum as for the preceding Examples. Human autoimmune serum (SLE: number 7 from Example 4, MCTD: number 11 from Example 4, and a normal control) and mouse serum from the inbred strain MRL with inborn susceptibility to auto-immune disease, and a control from the non-auto-immune BALB/C strain, are all diluted at 100, 1000 and 10000 in 10% horse serum in TBS, and the sheets incubated in the presence of these dilutions at ambient temperature, overnight.

The samples are then washed with TBS and incubated with a 1/1000 dilution in TBS-10% horse serum of peroxidase coupled rabbit anti-human immunoglobulins for the human sera and rabbit anti-mouse immunoglobulins for the mouse sera. The last two detection antisera are obtained from DAKO, Copenhagen, Denmark. They are then incubated for a further 2 hours at ambient temperature. The excess detecting antibody is then washed out with TBS and the bound antibody detected with the chloronaphthol reaction, as in Example 5. The color is allowed to develop for a further 2 hours and the results interpreted.

Both the human autoimmune sera show significant rheumatoid factor down to the 1:1000 dilutions, and none is seen at any dilution in the control serum. The mice autoimmune serum show a positive reaction down to the 1:10000 dilution, and the control mouse serum show a borderline-detectable positive reaction with the 100-fold diluted serum. The assay thus detects the presence of the high titer anti-rabbit IgG antibodies in both the pathological human and mouse sera. Immune complexes are also detected in the pathological sera at titers of approximately 10 times the control sera. High titer circulating immunecomplexes are found in the auto-immune mouse sera and the human MCTD and SLE sera. Further examples with a collection of two hundred human SLE sera and 20 individuals MRL mice with sera samples taken throughout their life-time, support these results.

The conditions described in this Example thus provide a workable system for detecting rheumatoid factors and immuno-complexes in both clinical diagnosis and animal model systems.

Example 10: Different microporous materials as supports for the dot immuno-binding assay A variety of microporous support materials are used, and 0.5 µl samples of antigens are applied as in the preceding Examples:

Supports: (1). New England Nuclear Cor., Boston, Mass. USA "Gene Screen" (microporous polyamide)

(2). Gelman (Gelman Sciences Inc., Ann-Arbor, Michigan, USA) Teflon HT450 (0.45 µ), an aromatic polysulfone copolymer for high temperature use, (3). Gelman Metricel GN6 "mixed cellulose ester" (0.45 µ), (4). Gelman Metricel GN6 cellulose triacetate (0.45 µ), (5). Schleicher & Schuell (Schleicher & Schuell GmbH, Dassel, W. Germany) nitrocellulose, (0.15 µ) BA 80/1, (6). Schleicher & Schuell nitrocellulose (0.45 µ) BA 85/1

(7). Schleicher & Schuell nitrocellulose (0.8 µ) AE 91/1

(8). Schleicher a Schuell nitrocellulose (12 µ) AE 100

(9). Schleicher a Schuell cellulose acetate (0.45 µ) OE 67

(10). Schleicher & Schuell reconstituted cellulose (0.45 µ) RC 57

(11) FMC (Rockland, Maine, USA) agarose, "Sea plaque"

(12). Difco Noble agar (Difco Laboratory Inc., Detroit, Michigan, USA).

The last two are deposited on a rigid plastic support of FMC Corporation "Gel Bond" according to the manufacturer's instructions, achieving a layer of 0.5 mg/cm$^2$. This last is done by applying 1 ml of molten agar or agarose on the surface in a 5 cm circle, and drying under an infra red lamp. When the agar is re-hydrated, it develops a porous structure.

The following antigens are applied in 0.5 µl aliquots as in the previous Examples, air dried, and subjected to the same protocol with the use of a human SLE serum (number 7 from Example 4):

(A). Native DNA (0.4 mg/ml)

(B). Denatured DNA (0.4 mg/ml)

(C). Influenza virus mixture (Undiluted Sandovac vaccine)

(D). Human IgG, 1 µg/ml in 1 mg/ml Bovine serum albumin (E). Human IgG, 10 µg/ml,in 1 mg/ml Bovine serum albumin (F). Human IgG, 100 µg/ml in 1 mg/ml Bovine serum ablumin (G). 1 mg/ml Bovine serum albumin.

TBS is the solvent as elsewhere.

After addition of the DNA samples, and before addition of the remainder, the blots are baked at 80° for two hours.

The following results are obtained and are compared with the standard system using Millipore of 0.45 μ pore size:

| Support | Results |
|---|---|
| (1) | Faintly visible A, C and F. Other dots negative. |
| (2) | A, B and C stain, D, E, F and G negative. |
| (3) | All dots positive, D, E and F show a series of graded intensity. |
| (4) | A and C faintly positive, all others negative. Background higher. |
| (5) | No significant difference from Millipore. |
| (6) | Exactly same as Millipore of same porosity. |
| (7) | D does not stain, otherwise as Millipore. |
| (8) | A, B and C stain, D, E, F fainter than Millipore. |
| (9) | A, C and F stain faintly. Others negative. |
| (10) | A and B positive, C faint, others negative. |
| (11) | A, B and C positive but faint, D, E, F borderline visible. |
| (12). | A, B and C positive, D, E and F weakly positive. | and dilutions (as indicated in parenthesis) in TBS are applied in the same kind of array as in preceding Examples, to Millipore nitrocellulose (0.45 μ) with a grid printed on it as in preceding Examples.

(1). Adenovirus (⅕), (2). Chlamydia (½), (3). Cytomegalovirus (undiluted) (3a). Cytomegalovirus control negative antigen (undiluted) (4). Influenza A (¼), (5). Influenza B (½), (6). Parainfluenza 1 (undiluted), (7). Parainfluenza 2 (undiluted), (8). Parainfluenza 3 (undiluted), (8a). Influenza control negative antigen (undiluted), (9). Mycoplasma (½) (10). Q Fever (½), (11). Respiratory syncytial Virus (½), and in addition 4 standards of human IgG (Nordic) at 10, 4,65, 2.15 and 1 μg/ml in TBS and 1 mg/ml bovine serum albumin. These are then assayed as in previous Examples with serum diluted at 1/100, 1/1000 and 1/10000 in TBS 10% horse serum, by the chloronaphthol method, using a 1:1000 dilution of peroxidase coupled goat anti-human IgG (Nordic). The results for sera provided as positive control sera, also by Intitut Virion, are listed in the following Table.

| serum code | Summary of respiratory virus antibody profiles obtained by dot-immuno assay. Titer of antibody in μg/ml in original serum obtained with antigen | | | | | | | | | | |
|---|---|---|---|---|---|---|---|---|---|---|---|
| | 1 | 2 | 3 | 4 | 5 | 6 | 7 | 8 | 9 | 10 | 11 |
| 1 | 0.1 | <0.03 | 0 | <0.03 | 0.15 | 0.15 | 0.03 | 0.15 | 0.1 | 0.03 | 0.33 |
| 2 | 0.07 | <0.03 | 0.07 | 0.03 | 0.15 | 0.07 | 0.07 | 0.07 | 0 | 0 | 0.33 |
| 3 | 0.03 | 0 | 0 | <0.03 | 0.15 | 0.15 | 0,07 | 0.07 | 0.03 | 0 | 0.33 |
| 4 | 0.07 | 0.15 | 0.07 | <0.03 | 0.15 | 0.15 | 0.15 | 0.07 | 0.03 | 0 | 0.72 |
| 5 | 0.03 | 0 | 0.07 | <0.03 | 0.03 | 0.07 | 0.07 | 0.07 | 0 | 0 | 0.72 |
| 6 | 0.07 | 0.03 | 0 | <0.03 | 0.15 | 0.1 | 0.07 | 0.07 | 0 | <<0.03 | 0.72 |
| 7 | 0.07 | 2.3 | <0.03 | <0.03 | 0.03 | 0.15 | 0.07 | 0.07 | 0.1 | <0.03 | 0.33 |
| 8 | 0.03 | <0.03 | 0 | <0.03 | 0.03 | 0.15 | 0.07 | 0.07 | 0.5 | 3.3 | 0.33 |
| 9 | 0.03 | 0.03 | 0 | <0.03 | 0.03 | 0.03 | 0.07 | 0.07 | 0.03 | <0.03 | 1.5 |
| 10 | 0.03 | <<0.03 | 0.15 | <<0.03 | 0.03 | 0.07 | 0.07 | 0.07 | 0.03 | 0 | 0.33 |
| 11 | 0.03 | <<0.03 | 0 | <<0.03 | 0.03 | 0 | 0.07 | 0.07 | 0 | 0 | 0.33 |
| 12 | <0.03 | <<0.03 | 0 | <<0.03 | 0.03 | 0.15 | 0.07 | 0.07 | 0 | 0 | 0.33 |
| 13 | 0.03 | <<0.03 | 0.03 | <0.03 | 0.07 | 0.07 | 0.07 | 0.07 | 0.72 | <<0.03 | <<0.33 |
| 14 | 0.03 | 0.03 | 0.03 | 0.03 | 0.07 | 0.07 | 0.07 | 0.07 | 0.1 | 0.03 | 0.72 |
| 15 | 0.03 | <0.03 | 0.15 | <<0.03 | 0.15 | 0.15 | 0.07 | 0.07 | 0.1 | 0.03 | 0.03 |
| 16 | 0 | <<0.03 | 0 | <0.03 | 0.15 | 0.5 | 0.07 | 3.3 | 0 | 0.33 | 3.3 |
| 17 | 0 | <<0.03 | 0 | <0.03 | 0.15 | 0.5 | 0.07 | 3.3 | 0 | 0.33 | 3.3 |
| 18 | 0.03 | <<0.03 | 0.07 | <0.03 | <0.03 | 0.33 | 0.07 | 1.5 | 0.15 | 0.07 | 0.7 |
| 19 | 0.07 | <<0.03 | 0.03 | <0.03 | 0.07 | 0.1 | 0.07 | 0.07 | 0.07 | 0.03 | 0.33 |
| 20 | <0.03 | 0.5 | 0.03 | <0.03 | 0.07 | 0.1 | 0.07 | 0.07 | 0.03 | 0.03 | 0.33 |
| 21 | <0.03 | <0.03 | 0.03 | <0.03 | 0.03 | 0.03 | 0.07 | 0.07 | 0.03 | 0.33 | 0.33 |
| 22 | 0.03 | 0.5 | 0 | <0.03 | 0.03 | 0.03 | 0.03 | 0.07 | 0.03 | 0.33 | 0.33 |
| 23 | 0.03 | <0.03 | 0.03 | <0.03 | 0.07 | 0.07 | 0.03 | 0.07 | 0.15 | 0.33 | 0.33 |
| 24 | 0.03 | 0.03 | 0.33 | <0.03 | <0.03 | 0.07 | 0.03 | 0.07 | 0.15 | 0.03 | 0.7 |
| 25 | 0.03 | 0.15 | 0 | <0.03 | 0.03 | 0.07 | 0.03 | 0.07 | 0.03 | 0.15 | 0.33 |
| 26 | <<0.03 | 0.07 | 0 | <0.03 | 0.07 | 0.03 | 0.07 | 0.07 | 0.07 | <<0.03 | 0.15 |

Agar has the merit of being easily coated on to a robust support and is transparent, so lending itself to quantitation by transmission instead of the reflectance measurements as in Example 5.

Example 11: Respiratory virus antibody profiles by multi-dot assay

This Example is similar to Example 3, except that the selection of antigens is based on a group of respiratory viruses which are commonly requested for diagnostic purposes as a group which are difficult to distinguish by symptoms alone. This group of antigens are obtained from Institut Virion, Zürich, and 0.5 μl of tile following antigens No antigens provided as negative control give any positive reaction with any serum.

Example 12: Comparison of dot immunobinding assays with complement fixation assays for obtaining respiratory virus antibody profiles in sera Complement fixation assays are carried out on the same set of sera as in Example 11, and with the same group of antigens from Institut Virion, using their materials and described procedure for complement fixation. The sera are classified in groups of the same titer, and then listed in descending order of titer. The vertical lines in the table below are the groupings according to titer. The underlined sera are those provided as positive control sera for that antigen.

Correlation of respiratory virus antibody profiles from dot immuno assays with corresponding data from complement fixation assays.
In each case, the left hand column is the order of titers for sera by the dot assay and the right hand column the order by the complement fixation assays. The sera underlined are those which were provided as part of the kit as control positive for that particular antigen.

| Adenovirus | | Ornithosis | | Influenza A | | Influenza B | | Para influenza 1 | |
|---|---|---|---|---|---|---|---|---|---|
| 1 | 19 | 7 | 7 | 2 | 14 | 1 | 16 | 16 | 16 |
| 2 | 6 | 20 | 25 | 14 | 2 | 2 | 17 | 17 | 17 |
| 4 | 7 | 22 | 20 | 1 | 5 | 3 | 18 | 18 | 18 |
| 6 | 9 | 4 | 1 | 3 | 9 | 4 | 15 | 1 | 25 |
| 7 | 8 | 25 | 2 | 4 | 4 | 6 | 19 | 3 | 7 |
| 19 | 1 | 26 | 3 | 5 | 7 | 15 | 25 | 4 | 8 |
| 3 | 2 | 6 | 4 | 6 | 21 | 16 | 4 | 7 | 11 |
| 5 | 5 | 24 | 5 | 7 | 25 | 17 | 3 | 8 | 12 |
| 8 | 25 | 1 | 6 | 8 | 1 | 18 | 7 | 12 | 1 |
| 9 | 21 | 2 | 8 | 9 | 6 | 13 | 20 | 15 | 2 |
| 10 | 3 | 8 | 9 | 13 | 8 | 19 | 6 | 6 | 3 |
| 13 | 4 | 14 | 10 | 16 | 10 | 20 | 1 | 19 | 4 |
| 14 | 15 | 15 | 11 | 17 | 3 | 23 | 9 | 20 | 5 |
| 15 | 18 | 21 | 12 | 18 | 11 | 26 | 21 | 2 | 6 |
| 18 | 10 | 23 | 13 | 19 | 12 | 14 | 8 | 5 | 9 |
| 22 | 11 | 9 | 14 | 20 | 13 | 5 | 2 | 10 | 10 |
| 23 | 12 | 10 | 15 | 21 | 15 | 7 | 5 | 13 | 13 |
| 24 | 13 | 11 | 16 | 22 | 16 | 8 | 10 | 14 | 14 |
| 11 | 14 | 12 | 17 | 23 | 17 | 9 | 11 | 23 | 15 |
| 12 | 16 | 13 | 18 | 24 | 18 | 10 | 12 | 24 | 19 |
| 20 | 17 | 16 | 19 | 25 | 19 | 11 | 13 | 25 | 20 |
| 21 | 20 | 17 | 21 | 26 | 20 | 12 | 14 | 26 | 21 |
| 25 | 22 | 18 | 22 | 10 | 22 | 21 | 22 | 9 | 22 |
| 26 | 23 | 19 | 23 | 11 | 23 | 22 | 23 | 21 | 23 |
| 16 | 24 | 3 | 24 | 12 | 24 | 24 | 24 | 22 | 24 |
| 17 | 26 | 5 | 26 | 15 | 26 | 25 | 26 | 11 | 26 |

| Para-influenza 2. | | Para-influenza 3. | | Mycoplasma | | Q Fever | | Respiratory syncytial virus | |
|---|---|---|---|---|---|---|---|---|---|
| 4 | 25 | 16 | 16 | 13 | 9 | 8 | 8 | 16 | 9 |
| 2 | 15 | 17 | 17 | 8 | 1 | 16 | 21 | 17 | 16 |
| 3 | 23 | 18 | 18 | 18 | 7 | 17 | 16 | 9 | 17 |
| 5 | 4 | 1 | 25 | 19 | 13 | 21 | 17 | 4 | 25 |
| 6 | 7 | 2 | 7 | 20 | 25 | 22 | 1 | 5 | 6 |
| 7 | 10 | 3 | 21 | 24 | 19 | 23 | 2 | 6 | 1 |
| 8 | 6 | 4 | 9 | 1 | 3 | 25 | 3 | 14 | 2 |
| 9 | 8 | 5 | 1 | 7 | 18 | 18 | 4 | 18 | 5 |
| 10 | 9 | 6 | 5 | 14 | 20 | 1 | 5 | 24 | 7 |
| 11 | 12 | 7 | 11 | 15 | 8 | 14 | 6 | 1 | 8 |
| 12 | 21 | 8 | 15 | 26 | 10 | 15 | 7 | 2 | 10 |
| 13 | 1 | 9 | 2 | 9 | 15 | 19 | 9 | 3 | 11 |
| 14 | 2 | 10 | 3 | 3 | 21 | 20 | 10 | 7 | 18 |
| 15 | 3 | 11 | 4 | 4 | 2 | 24 | 11 | 8 | 21 |
| 16 | 5 | 12 | 6 | 10 | 4 | 7 | 12 | 10 | 3 |
| 17 | 11 | 13 | 8 | 21 | 5 | 9 | 13 | 11 | 4 |
| 18 | 13 | 14 | 10 | 22 | 6 | 6 | 14 | 12 | 12 |
| 19 | 14 | 15 | 12 | 23 | 11 | 13 | 15 | 13 | 13 |
| 20 | 16 | 19 | 13 | 25 | 12 | 26 | 18 | 15 | 14 |
| 21 | 17 | 20 | 14 | 2 | 14 | 2 | 19 | 19 | 15 |
| 1 | 18 | 21 | 19 | 3 | 16 | 3 | 20 | 20 | 19 |
| 22 | 19 | 22 | 20 | 4 | 17 | 4 | 22 | 21 | 20 |
| 23 | 20 | 23 | 22 | 11 | 22 | 10 | 23 | 22 | 22 |
| 24 | 22 | 24 | 23 | 12 | 23 | 11 | 24 | 23 | 23 |
| 25 | 24 | 25 | 24 | 16 | 24 | 12 | 25 | 25 | 24 |
| 26 | 26 | 26 | 26 | 17 | 26 | 5 | 26 | 26 | 26 |

It can be seen from the tables that in almost all cases, the positive sera fall into approximately the same rank, and there are even cases where both assays demonstrate that the serum provided as positive is in fact negative or of low titer. All assays correlate rather well. The reasons for the exceptions may be that the 2 assay systems recognize different classes of antibodies and that the antigen is presented to the antibody in a very different form in the two assays.

Example 13: Use of a dot assay for the typing of monoclonal antibodies.

Monoclonal antibodies to ribosomal proteins from chick liver are prepared by the same procedure as in Example 8, and the specificity of the antibodies determined by the method published by Towbin et al (*Proc. Nat. Acad. Sci. U.S.*, 76, 4350–4354 (1979)). The supernatants from the hybridoma cultures are tested for the antibody type by the following dot assay. Type-specific goat anti-mouse immunoglobulin antibodies from Nordic are dissolved according to the manufacturer's instructions, diluted 30-fold and 1 µl aliquots dotted on to nitrocellulose, the strips blocked with horse serum as in Example 1, incubated overnight at room temperature with undiluted hybridoma supernatants, then bound antibody detected with immun-peroxidase staining as in Example 1. The results are shown in the following Table:

| Monoclonal antibody | Stain with antibody against | |
|---|---|---|
|  | IgG | IgM |
| Anti-S6 | + | − |
| Anti-L7 | − | + |
| Anti-L18a | + | − |
| Anti-P1/P2 | − | + |
| Anti-rRNA | − | + |

The monoclonal antibodies are designated according to the ribosomal protein they react with, according to internationally recognized nomenclature. Anti-rRNA is directed against ribosomal RNA. The typing in the table is confirmed in separate experiments where the antibodies are analysed on sucrose gradients: the IgG has a sedimentation constant of 7S, the IgM of 19S.

This Example shows that antibodies can be mounted on the support, and used to detect their respective antigen, provided a suitable detection system is available. This assay procedure is of utility in quantitating the amounts of individual antibody classes in human sera, as is frequently required for clinical analyses. This system permits the construction of a kit for the analysis and quantitation of all antibody classes simultaneously in one operation.

Example 14: Kits for immunological analysis.

Devices are constructed by dotting aliquots of 0.5 µl of the antigens of the preceding Examples. The antigen solutions are dotted in parallel rows on sheets of Millipore (0.45 micron pore size) having a grid printed on it, as in preceding Examples. These are treated with 10% horse serum, as elsewhere, to block the non-specific binding sites, and air-dried. The sheets are cut into strips such that each strip contains one of each antigen dot, and sealed into plastic pages. Reagents for performing the immunological analysis are prepared as follows.

A. TBS containing 10% horse serum is lyophilized in 100 ml lots.

B. Goat anti-human immunoglobulins is diluted 1:1000 in TBS containing 10% horse serum and lyophilized in 100 ml lots.

C. TBS is lyophilized in 100 ml lots.

D. 4-chloro-1-naphthol is dispensed in 9 mg portions and sealed into ampoules.

E. $H_2O_2$ (30%) is dispensed in 0.1 ml portions and sealed into ampoules.

After indefinite storage, the above kits may be used as follows for the analysis of unknown antibodies in serum, corresponding to the methodology of the preceding Examples. One portion each of A, B and C is reconstituted with 100 ml of distilled water. A is then used in the dilution of the unknown sera, B for the indicator antibody binding reaction, and one lot of reconstituted C, together with one ampoule each of D and E make up the color reaction mixture. Other lots of C are reconstituted as needed for the washes after each stage of antibody binding.

The same results are obtained as in the preceding Examples.

What is claimed:

1. An immunological analysis device consisting of a porous sheet of nitrocellulose containing an array of preselected geometry of delimited absorption areas of at least one compound capable of specifically binding an antigen (antigen-reactive compound) which adheres tightly and does not spread out on the surface of said porous sheet, said array of preselected geometry being obtained in said porous sheet by applying liquid aliquots of said antigen-reactive compound to said porous sheet mechanically via direct contact, wherein residual absorption sited in said porous sheet are unsaturated or saturated by non-specific protein.

2. The device of claim 1 wherein said antigen-reactive compound is an immunoglobulin of human or animal origin or a binding fragment thereof for the detection and quantitation of rheumatoid factor.

3. The device of claim 1 wherein said antigen-reactive compound is a complement protein for the detection and quantitation of a circulating immune complex which circulating immune complex comprises an antigen-antibody complex.

4. The device of claim 1 wherein said porous sheet is from about 0.01 to about 0.5 mm thick.

5. The device of claim 4 wherein said porous sheet is about 0.1 mm thick.

6. The device of claim 1 wherein said nitrocellulose has about 3 nitric acid groups per 6 carbon atoms.

7. The device of claim 1 wherein said porous sheet has an average pore size of about 0.45 um.

8. The device of claim 1 wherein said array is an array of dots.

9. The device of claim 1 wherein said array is an array of microdots having diameters less than 2 mm.

10. The device of claim 1 wherein said array is an array of lines of width of 2 mm or less.

11. The device of claim 1 wherein said antigen-reactive compound is applied to said support by a capillary tube, pipette, syringe, or spray.

12. The device of claim 1 wherein said antigen-reactive compound is applied to said support in volumes of less than 1 ul.

13. The device of claim 1 wherein said residual adsorption area is saturated with a serum containing substance, wherein said substance is undiluted total serum or total serum diluted with sodium chloride.

14. The device of claim 1 wherein said antigen-reactive compound is reactive to an antigen, wherein said antigen is a constituent of human biopsy material, mammalian tissue, mammalian cells, body fluids, fungi, protozoa, metazoan parasites, bacteria, mycoplasma, or viruses.

15. A kit comprising the device of claim 1 and reagents of an indicator system in pre-aliquoted or dessicated form to allow detection of an antigen — antigen reactive compound complex.

16. The kit of claim 15 wherein said indicator is selected from the group consisting of A) antibodies capable of forming antigen-antibody complexes, wherein the antibody is radioactively labelled, conjugated with a fluorescent substance or conjugated with an enzyme capable of giving a color reaction with a suitable substrate, B) complement protein capable of binding to antigen-antibody complexes, wherein the complement protein is radioactively labelled, conjugated with a fluorescent substance or conjugated with an enzyme capable of giving color reaction with a suitable substrate, and C) complement protein and a further specific anti-complement antibody, wherein the antibody is radioactively labelled, conjugated with a fluorescent substance or conjugated with an enzyme capable of giving a color reaction with a suitable substrate.

17. The kit of claim 16, wherein said antigen-reactive compound is complement protein for the detection and quantitation of circulating immune complex which circulating immune complex comprises an antigen-antibody complex and wherein the indicator is a group A) antibody radioactively labelled, conjugated with a fluorescent substance or conjugated with an enzyme capable of giving a color reaction with a suitable substrate.

18. The kit of claim 15, wherein said antigen-reactive compound is an immunoglobulin of human or animal origin or a binding fragment thereof for the detection and quantitation of rheumatoid factor.

19. The kit of claim 15, comprising a multi-cavity plastic tray, lyophilized mixtures of indicator antibody, salts, buffers, carrier serum or protein, and pre-determined amounts of indicator enzyme chromogenic substrate, salts, buffers, and ampoules containing pre-measured volumes of liquid substrates, all in suitable packaging.

20. The kit of claim 15 wherein said reagents of said indicator system comprise a substrate, a cofactor or prosthetic group for an indicator enzyme, or a coupled series of enzymes.

21. The kit of claim 15, wherein the reagents of said indicator system comprise a covalent adduct between an antigen and a signalling molecule.

22. A method of immunological analysis comprising (a) incubating the device of claim 1 wherein residual absorption sites in said porous sheet are saturated by non-specific protein, with a sample containing an immunoglobulin or other antigen to be detected;

(b) incubating said device with a solution of an indicator selected from the group consisting of A) antibodies capable of forming antigen-antibody complexes, wherein the antibody is radioactively labelled, conjugated with a fluorescent substance or conjugated with an enzyme capable of giving a color reaction with a suitable substrate, B) complement protein capable of binding to antigen-antibody complexes, wherein the complement protein is radioactively labelled, conjugated with a fluorescent substance or conjugated with an enzyme capable of giving color reaction with a suitable substrate, and C) complement protein and a further specific anti-complement antibody, wherein the antibody is radioactively labelled, conjugated with a fluorescent substance or conjugated with an enzyme capable of giving a color reaction with a suitable substrate;

(c) when the antibody or complement protein of step (b) is conjugated with an enzyme, incubating said device with a solution of said suitable enzyme substrate; and (d) detecting the signal of said indicator of step (b).

23. The method of claim 22, wherein the incubation with a sample containing the immunogloblin or antigen to be detected is in the presence of non-specific proteins with regard to the immunoreactive compounds.

24. The method of claim 22, wherein the indicator is selected from the group consisting of radioactively labelled antibodies, antibodies conjugated with a fluorescent substance, and antibodies conjugated with an enzyme capable of giving a color reaction with a suitable substrate.

25. A method of claim 22, wherein the indicator is a horseradish peroxidase conjugated antibody.

26. An immunological analysis device consisting of a porous sheet of nitrocellulose containing an array of preselected geometry of delimited absorption areas of at least one antigen, which adheres tightly and does not spread out on the surface of said porous sheet, said array of preselected geometry being obtained in said porous sheet by applying liquid aliquots of said antigen to said porous sheet mechanically via direct contact, wherein residual absorption sites in said porous sheet are unsaturated or saturated by non-specific protein.

27. The device of claim 26 wherein said porous sheet is from about 0.01 to about 0.5 mm thick.

28. The device of claim 27 wherein said porous sheet is about 0.1 mm thick.

29. The device of claim 27 wherein said nitrocellulose has about 3 nitric acid groups per 6 carbon atoms.

30. The device of claim 27 wherein said porous sheet has an average pore size of about 0.45 um.

31. The device of claim 27 wherein said array is an array of dots.

32. The device of claim 27 wherein said array is an array of microdots having diameters less than 2 mm.

33. The device of claim 27 wherein said array is an array of lines of width of 2 mm or less.

34. The device of claim 26 wherein said antigen is applied to said support by a capillary tube, pipette, syringe, or spray.

35. The device of claim 26 wherein said antigen is applied to said support in volumes of less than 1 ul.

36. The device of claim 26 wherein said residual adsorption area is saturated with a serum containing substance, wherein said substance is undiluted total serum a total serum diluted with sodium chloride.

37. The device of claim 26 wherein said antigen is a constituent of human biopsy material, mammalian tissue, mammalian cells, body fluids, fungi, protozoa, metazoan parasites, bacteria, mycoplasma, or viruses.

38. A kit comprising the device of claim 26 and reagents of an indicator system in pre-aliquoted or dessicated form to allow detection of an antigen — antigen reactive compound complex.

39. The kit of claim 38 wherein said indicator is selected from the group consisting A) antibodies capable of forming antigen-antibody complexes, wherein the antibody is radioactively labelled, conjugated with a fluorescent substance or conjugated with an enzyme capable of giving a color reaction with a suitable substrate, B) complement protein capable of binding to antigen-antibody complexes, wherein the complement protein is radioactively labelled, conjugated with a fluorescent substance or conjugated with an enzyme capable of giving color reaction with a suitable substrate, and C) complement protein and a further specific anti-complement antibody, wherein the antibody is radioactively labelled, conjugated with a fluorescent substance or conjugated with an enzyme capable of giving a color reaction with a suitable substrate.

40. The kit of claim 38, comprising a multi-cavity plastic tray, lyophilized mixtures of indicator antibody, salts, buffers, carrier serum or protein, and pre-determined amounts of indicator enzyme chromogenic substrate, salts, buffers, and ampoules containing pre-measured volumes of liquid substrates, all in suitable packaging.

41. The kit of claim 38 wherein said reagents of said indicator system comprise a substrate, a cofactor or prosthetic group for an indicator enzyme, or a coupled series of enzymes.

42. The kit of claim 38, wherein the reagents of said indicator system comprise a covalent adduct between an antigen and a signalling molecule.

43. A method of immunological analysis comprising (a) incubating the device of claim 26 wherein residual absorption sites in said porous sheet are saturated by non-specific protein, with a sample containing an immunoglobulin to be detected;

(b) incubating said device with a solution of an indicator selected from the group consisting of A) antibodies capable of forming antigen-antibody complexes, wherein the antibody is radioactively labelled, conjugated with a fluorescent substance or conjugated with an enzyme capable of giving a color reaction with a suitable substrate, B) complement protein capable of binding to antigen-antibody complexes, wherein the complement protein is radioactively labelled, conjugated with a fluorescent substance or conjugated with an enzyme capable of giving color reaction with a suitable substrate, and C) complement protein and a further specific anti-complement antibody, wherein the antibody is radioactively labelled, conjugated with a fluorescent substance or conjugated with an enzyme capable of giving a color reaction with a suitable substrate;

(c) when the antibody or complement protein of step (b) is conjugated with an enzyme, incubating said device with a solution of said suitable enzyme substrate; and (d) detecting the signal of said indicator of step (b).

44. The method of claim 43, wherein the incubation with a sample containing the immunogloblin to be detected is in the presence of non-specific proteins with regard to the immunoreactive compounds.

45. The method of claim 43, wherein the indicator is selected from the group consisting of radioactively labelled antibodies, antibodies conjugated with a fluorescent substance, and antibodies conjugated with an enzyme capable of giving a color reaction with a suitable substrate.

46. A method of claim 43, wherein the indicator is a horseradish peroxidase conjugated antibody.

47. A method of producing an immunoassay device which comprises the steps of:

(a) applying droplets of substantially enriched aqueous solutions of antibodies of distinct specification to a substantially planar surface of a support, locating said droplets so that they cover small, discrete, closely spaced areas of the planar surface of the support and form an array;

(b) allowing said aqueous solutions of antibodies to remain on said areas of the surface for a period of time long enough for the antibodies in solution to be adsorbed to said areas of the surface to form discrete, antibody-coated areas;

(c) swiftly flooding the entire surface of the solid support with an aqueous solution of protein in order to block non-specific binding sites in areas of the surface of the solid support which surround the antibody-coated areas; and (d) washing and drying the device.

* * * * *